(12) United States Patent
Boettiger

(10) Patent No.: US 7,683,407 B2
(45) Date of Patent: Mar. 23, 2010

(54) STRUCTURE AND METHOD FOR BUILDING A LIGHT TUNNEL FOR USE WITH IMAGING DEVICES

(75) Inventor: Ulrich C. Boettiger, Boise, ID (US)

(73) Assignee: Aptina Imaging Corporation, Grand Cayman (KY)

( * ) Notice: Subject to any disclaimer, the term of this patent is extended or adjusted under 35 U.S.C. 154(b) by 253 days.

(21) Appl. No.: 11/193,450

(22) Filed: Aug. 1, 2005

(65) Prior Publication Data

US 2007/0023799 A1 Feb. 1, 2007

(51) Int. Cl.
*H01L 31/062* (2006.01)
*H01L 31/113* (2006.01)

(52) U.S. Cl. ..................................... 257/292
(58) Field of Classification Search .................. 257/53, 257/59, 185, 233, 292, E21.576–E21.579, 257/431–470, 655, E27.131–E27.133, E27.154, 257/E27.158, 225, E27.135, E21.584, 222, 257/E31.125; 438/57, 60
See application file for complete search history.

(56) References Cited

U.S. PATENT DOCUMENTS

| | | | |
|---|---|---|---|
| 6,198,087 B1 * | 3/2001 | Boon | 250/208.1 |
| 6,235,549 B1 * | 5/2001 | Bawolek et al. | 438/48 |
| 6,278,169 B1 * | 8/2001 | Sayuk et al. | 257/435 |
| 6,316,814 B1 * | 11/2001 | Nagata et al. | 257/435 |
| 6,335,540 B1 * | 1/2002 | Zhang | 257/53 |
| 6,812,539 B1 * | 11/2004 | Rhodes | 257/435 |
| 7,193,289 B2 * | 3/2007 | Adkisson et al. | 257/431 |
| 2004/0012029 A1 * | 1/2004 | Bawolek et al. | 257/98 |
| 2005/0285215 A1 * | 12/2005 | Lee et al. | 257/432 |

OTHER PUBLICATIONS

Yaung, et. al, "Air-Gap Guard Ring for Pixel Sensitivity and Crosstalk Improvement in Deep Sub-micron CMOS Image Sensor," IEEE, 2003.

* cited by examiner

*Primary Examiner*—Dao H Nguyen
*Assistant Examiner*—Tram H Nguyen
(74) *Attorney, Agent, or Firm*—Dickstein Shapiro LLP

(57) ABSTRACT

A pixel cell and imager device, and method of forming the same, where the pixel cell has a plurality of metallization and via layers formed over a photosensitive region. The metallization and via layers form a step-like light tunnel structure that augments the photosensitive region's ability to capture light impinging on the photosensitive region.

37 Claims, 12 Drawing Sheets

STRUCTURE AND METHOD FOR BUILDING A LIGHT TUNNEL FOR USE WITH IMAGING DEVICES

FIELD OF THE INVENTION

This invention relates generally to the field of semiconductor imaging devices, and more particularly, to a light tunnel for use in imaging devices.

BACKGROUND OF THE INVENTION

Solid-state image sensors, also known as imagers, were developed in the late 1960s and early 1970s primarily for television image acquisition, transmission, and display. An imager absorbs incident radiation of a particular wavelength (such as optical photons, x-rays, or the like) and generates an electrical signal corresponding to the absorbed radiation.

There are a number of different types of semiconductor-based imagers, including charge coupled devices (CCD's), photodiode arrays, charge injection devices (CID's), hybrid focal plane arrays, and complementary metal oxide semiconductor (CMOS) imagers. Current applications of solid-state imagers include cameras, scanners, machine vision systems, vehicle navigation systems, video telephones, computer input devices, surveillance systems, auto focus systems, star trackers, motion detector systems, image stabilization systems, and other image acquisition and processing systems.

Solid-state imagers typically consist of an array of pixel cells. Each pixel cell contains a photosensor that produces a signal corresponding to the intensity of light impinging on the photosensor. When an image is focused on the array of pixel cells, the combined signals may be used, for example, to display a corresponding image on a monitor or otherwise used to provide information about the optical image.

The photosensors are typically phototransistors, photoconductors or photodiodes, in which the conductivity of the photosensor, or the charge stored in a diffusion region, corresponds to the intensity of light impinging on the photosensor. The magnitude of the signal produced by each pixel, therefore, is proportional to the amount of light impinging on the photosensor. Accordingly, it is important that all of the light directed to the photosensor impinges on the photosensor rather than becoming reflected or refracted. If light does not impinge on the correct photosensor, optical crosstalk between pixels may occur.

For example, optical crosstalk may exist between neighboring photosensors in a pixel array of a solid-state imager. In an idealized photosensor, a photodiode for example, light enters only through the surface of the photodiode that directly receives the light stimulus. In reality, however, light intended for neighboring photosensors also enters the photodiode, in the form of stray light, through the sides of the photosensor structure for example. Reflection and refraction within the photosensor structure can give rise to stray light, which is referred to as optical crosstalk.

Optical crosstalk can bring about undesirable results in images that are produced. The undesirable results can become more pronounced as the density of pixels in imager arrays increases, and as pixel size correspondingly decreases. The shrinking pixel sizes make it increasingly difficult to focus incoming light on the photosensor of each pixel.

Optical crosstalk can manifest as a blurring or reduction in contrast in images produced by a solid-state imager. In essence, crosstalk in an image sensor array degrades the spatial resolution, reduces overall sensitivity, causes color mixing, and leads to image noise after color correction. As noted above, image degradation can become more pronounced as pixel and device sizes are reduced. Furthermore, degradation caused by optical crosstalk is more conspicuous at longer wavelengths of light. Light at longer wavelengths penetrates more deeply into the silicon structure of a pixel cell, providing more opportunities for the light to be reflected or refracted away from its intended photosensor target.

One method to combat optical crosstalk is to employ a micro-lens array with the imager pixel array. The micro-lenses focus light onto respective photosensors, thereby increasing the amount of light energy impinging on each photosensor. Despite the use of micro-lens arrays, a large amount of incident light is still not directed efficiently onto the photosensors due to the geometry of the micro-lens array. As a result, the ability of a photosensor array to accurately reproduce an image varies between pixels across the array.

Another method to reduce optical crosstalk, in an imaging device, is the use of light shields. Light shields are formed in layers fabricated above the light-admitting surface through which the photosensor directly receives light stimulus. The light shield layers generally include metal and other opaque materials.

The light shields generally are formed as part of the uppermost layers of the solid-state imager array. Light shields have been formed, for example, in multi-level metal interconnect layers (e.g., Metal 1, Metal 2, or, if utilized, Metal 3 layers) of the photosensor's integrated circuitry. Light shields formed in such upper fabrication layers have inherent drawbacks, however. For example, metallization layers dedicated to light shielding are limited in their normal use as conductive connections for the imager array.

Additionally, light shields formed in upper device layers are separated from the light-admitting surface of the photosensor by several light transmitting layers. Moreover, the light shields are imperfect, and allow some light to pass into the light transmitting layers. Consequently, optical crosstalk still occurs through the light transmitting layers between the photosensor and the light shields. Having the light shields spaced apart from the surface of the photosensor can also increase light piping and light shadowing in the photosensors, leading to further errors in imager function.

Another method of reducing optical crosstalk uses optical waveguides, i.e., light tunnels. Optical waveguides are structures used for spatially confining light. For instance, optical waveguides can be used to reduce the detrimental affects associated with light shields such as light piping and light shadowing. Optical waveguides, however, are not currently used to focus light directly on the photosensor. Moreover, the optical waveguide structures that are currently employed, require additional processing steps, adding to the complexity and costs of imager fabrication.

Accordingly, solid-state imagers would benefit from a more efficient and effective optical waveguide structure that can focus light directly onto the photosensor, similar to a micro-lens. Of particular benefit would be a light tunnel that can be incorporated into current imagers to better mitigate optical crosstalk without added complexity to the manufacturing process.

BRIEF SUMMARY OF THE INVENTION

In general, the present invention, in various exemplary embodiments, provides fabrication methods and resulting pixel cell structures in which individual metallization and via layers, normally used in pixel cell fabrication, are patterned into sections that collectively, form a light tunnel to guide and focus light on a corresponding photosensitive region.

In one exemplary embodiment, a plurality of metallization and via layers, each comprising a conductive interconnect pattern and an interlevel dielectric are formed over a photosensor. The metallization and via layers are formed to have apertures of varying widths. The aperture closest to the photosensor region is smaller than the aperture at the topmost metallization and via layer. The metallization and via layers form a light tunnel structure that physically augments the light collecting capabilities of the pixel. The light tunnel can be formed to have a shape substantially similar to the photosensor region.

According to another embodiment of the invention, a method of forming a light tunnel for a pixel cell provides at least two metallization layers and a single via layer. A first metallization layer is formed over a photosensor region. A patterned photoresist is formed over the first metallization layer to form a first aperture having a width substantially similar to the width of the photosensor region. A via layer is formed over the first metallization layer to have an aperture larger than the first metallization layer's aperture. A second metallization layer is formed over the first patterned metallization and via layer. A patterned photoresist is formed over the second metallization layer to form a third aperture that is larger than the first and second apertures. Together, the first and second patterned metallization layers and via layer form a light tunnel that focuses light on the photosensor region.

According to another embodiment of the present invention, a plurality of metallization and via layers, each comprising a conductive interconnect pattern and an interlevel dielectric, are formed over an anti-reflective layer. The anti-reflective layer is formed over portions of the photosensor. A transparent dielectric layer is formed over the anti-reflective layer comprising metal contact rings. The metallization and via layers are formed to have apertures of varying widths over the transparent dielectric and anti-reflective layers. The aperture closest to the photosensor region is smaller than the aperture at the topmost metallization and via layer. The metallization and via layers form a light tunnel structure that physically augments the light collecting capabilities of the pixel. The light tunnel can be formed to have a shape substantially similar to the photosensor region.

According to another embodiment of the invention, a method of forming a light tunnel for a pixel cell is provided with at least two metallization layers and an anti-reflective layer. An anti-reflective layer is formed over a photosensor region. A transparent dielectric layer is formed over the anti-reflective layer. Metal contact rings are formed in the transparent dielectric layer having a width that is substantially similar to the width of the photosensor ring. A first metallization layer is formed over the transparent dielectric ring. A patterned photoresist is formed over the first metallization layer to form a first aperture having a width substantially similar to the width of the metal contact rings. A second metallization layer is formed over the first patterned metallization layer. A patterned photoresist is formed over the second metallization layer to form a second aperture that is larger than the first aperture. Together, the first and second patterned metallization layers form a light tunnel that focuses light onto the photosensor region.

BRIEF DESCRIPTION OF THE DRAWINGS

The above and other advantages and features of the invention will be more clearly understood from the following detailed description which is provided in connection with the accompanying drawings.

FIG. 10 shows a stage of fabrication of a circuit subsequent to that shown in FIG. 9a.

DETAILED DESCRIPTION OF THE INVENTION

Figure 1:
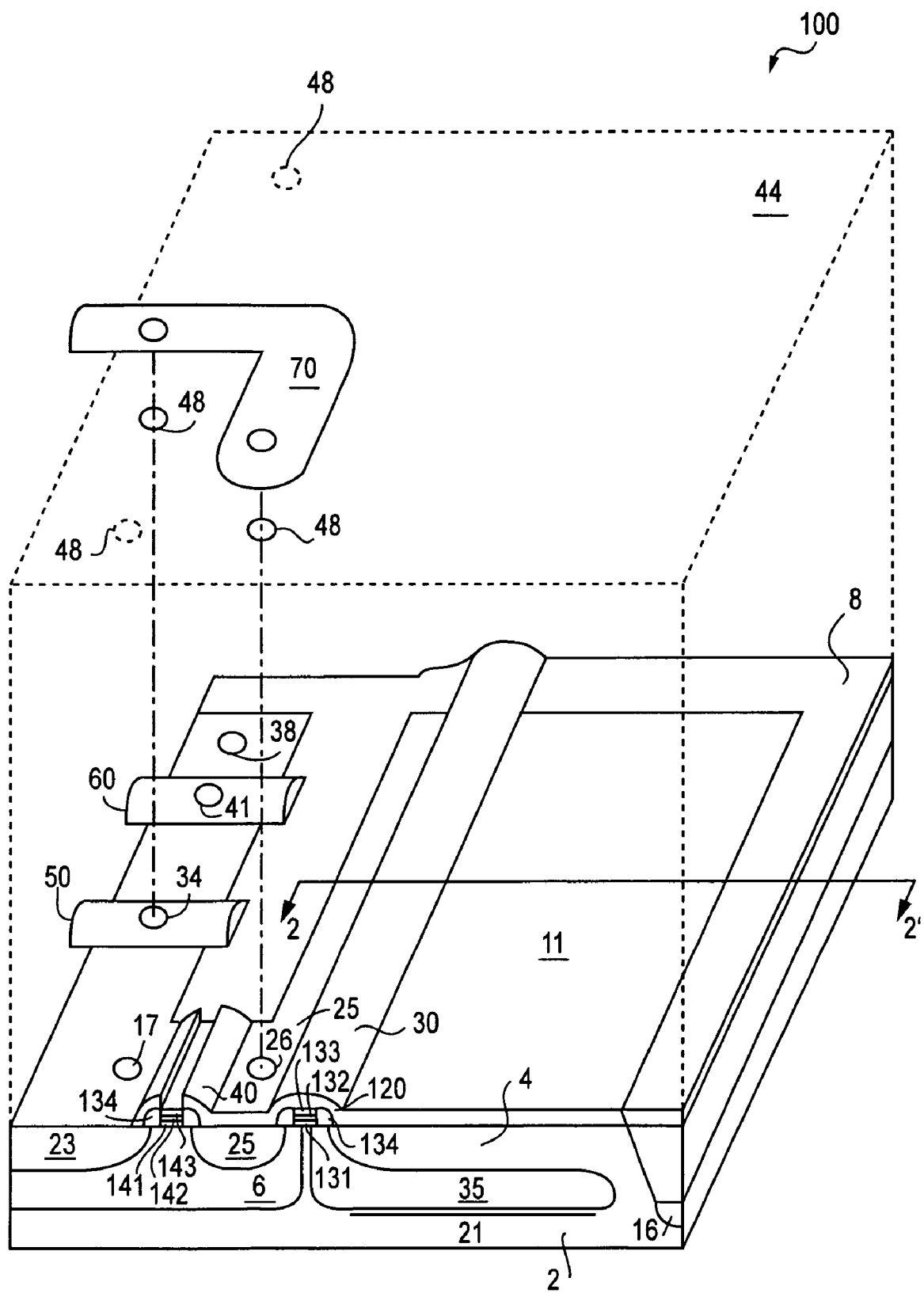
FIG. 1 is an exploded perspective view of a pixel cell in accordance with the invention.

In the following detailed description, reference is made to the accompanying drawings which form a part hereof and illustrate specific exemplary embodiments by which the invention may be practiced. It should be understood that like reference numerals represent like elements throughout the drawings. These embodiments are described in sufficient detail to enable those skilled in the art to practice the invention. It is to be understood that other embodiments may be utilized, and that structural, logical, and electrical changes may be made without departing from the spirit and scope of the present invention.

The term "substrate" is to be understood as including silicon-on-insulator (SOI) or silicon-on-sapphire (SOS) technology, doped and undoped semiconductors, epitaxial layers of silicon supported by a base semiconductor foundation, and other semiconductor structures. Furthermore, when reference is made to a "substrate" in the following description, previous process steps may have been utilized to form regions or junctions in the base semiconductor structure or foundation. In addition, the semiconductor need not be silicon-based, but could be based on silicon-germanium, germanium, or gallium arsenide, for example.

The term "light" refers to electromagnetic radiation that can produce a visual sensation (visible light) as well as electromagnetic radiation outside of the visible spectrum. In general, light as used herein is not limited to visible radiation, but refers more broadly to the entire electromagnetic spectrum, particularly electromagnetic radiation that can be transduced by a solid-state photosensor into a useful electrical signal.

The term "layer" refers to both a single layer and multiple layers, or strata. The term 'layer' can be understood to refer to a structure that includes multiple layers. Typically, similar fabrication steps and processes, such as patterning and etching, are applied to all layers in the structure. Adjacent layers can be patterned and etched simultaneously.

The terms "pixel(s)" or "pixel cell(s)" refers to a photo-element unit cell containing a photoconversion device and associated transistors for converting electromagnetic radiation to an electrical signal. The pixel cells discussed herein are illustrated and described as 4T (4 transistors) pixel cell circuits for the sake of example only. It should be understood that the invention is not limited to a four transistor (4T) pixel cell, but may be used with other pixel cell arrangements having fewer (e.g., 3T) or more (e.g., 5T) than four transistors.

Although the invention is described herein with reference to the architecture and fabrication of one or a limited number of pixels, it should be understood that this is representative of a plurality of pixel cells as typically would be arranged in an imager array having pixel cells arranged, for example, in rows and columns.

In addition, although the invention is described below with reference to a pixel cell for a CMOS imager, the invention has applicability to other solid-state imaging devices using a pixel cell (e.g., a CCD). The following detailed description is, therefore, not to be taken in a limiting sense, and the scope of the present invention is defined only by the appended claims.

Generally, horizontal metallic interconnection or wire lines are formed to connect devices within a pixel cell 100 (FIG. 1) and a pixel cell 100 with external circuitry. The horizontal metallic interconnections are conducting layers that permit an electrical current to be delivered to and from pixel cell 100. Since the integrated circuitry needed for a solid-state imager is usually built-up three-dimensionally on substrate 2 in order to increase the packing density and so forth, multi-level metallization layers are generally necessary and employed in which inter-level dielectric layers, also known as via layers, are interposed between different metallization levels formed on substrate 2.

Vias, also referred to as "vertical interconnects," are used to electrically connect different horizontal levels of metallization. The via is a via hole or through-hole filled with a conductor material that extends through a dielectric material, i.e., via level layer, interposed between surfaces of two separate horizontal metallization levels. The metallization process is repeated as needed to form additional levels and to form a plurality of similar horizontal and vertical conductive interconnections. Among other things, the yield, performance and reliability of the semiconductor device critically depend on the stability and integrity of the vias. Applicant provides a novel structure and method to use different metallization and via layers to create a light tunnel 103 for use in a pixel cell (FIGS. 2-13).

Figure 2:
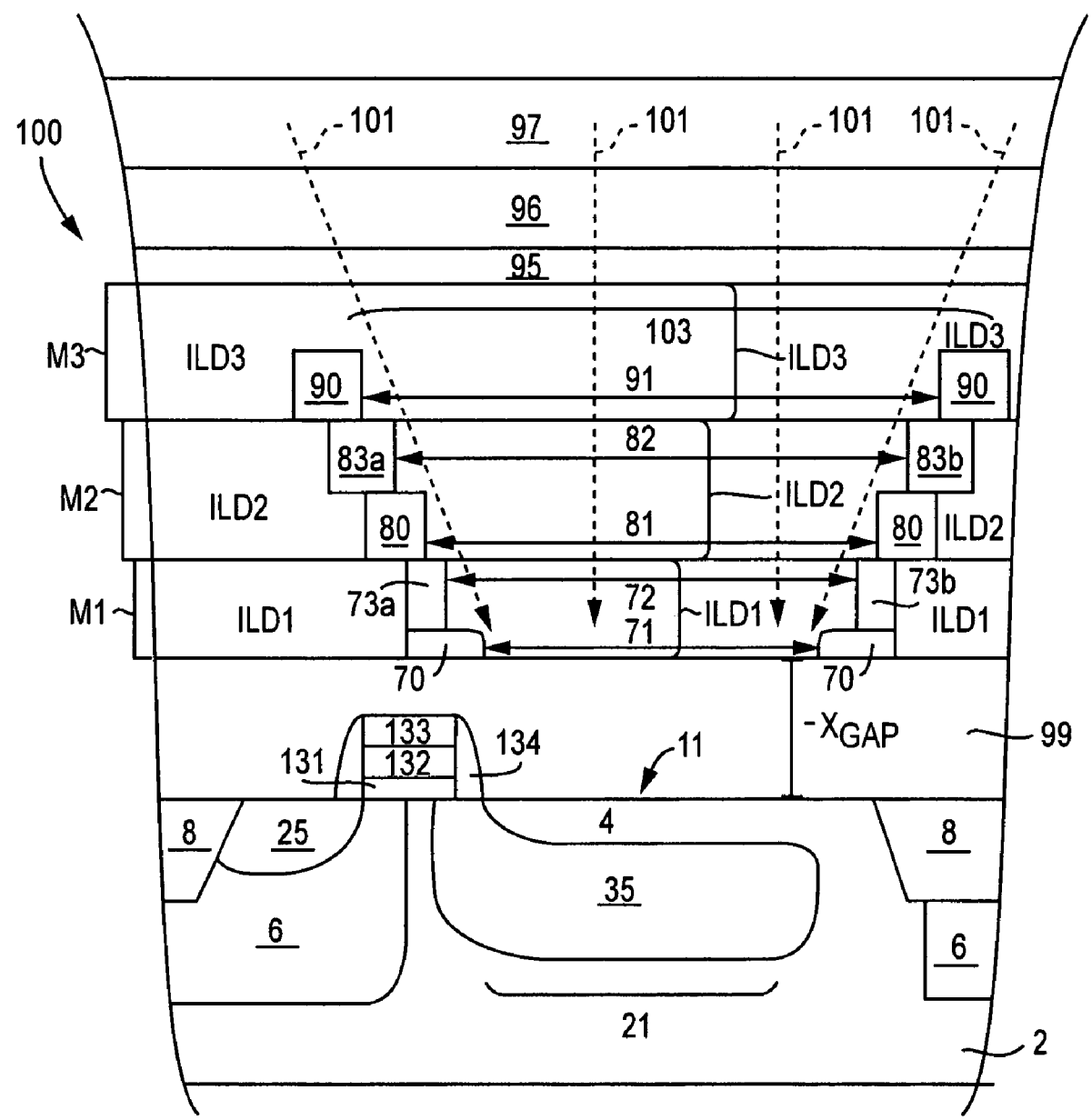
FIG. 2 is a partial cross-sectional view of the pixel cell of FIG. 1 through line 2-2', also showing additional conductive interconnect layers.
Figure 3A:
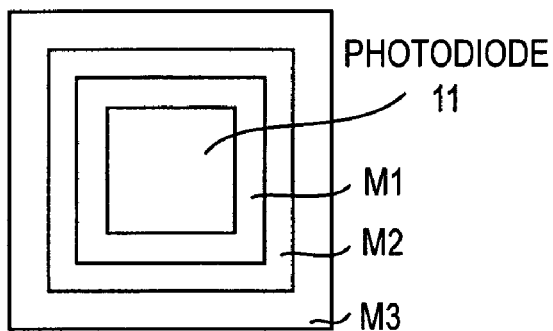
FIGS. 3A-3D are top down views of a photodiode from the pixel cell of FIG. 2, also showing additional conductive interconnect layers.
Figure 3B:
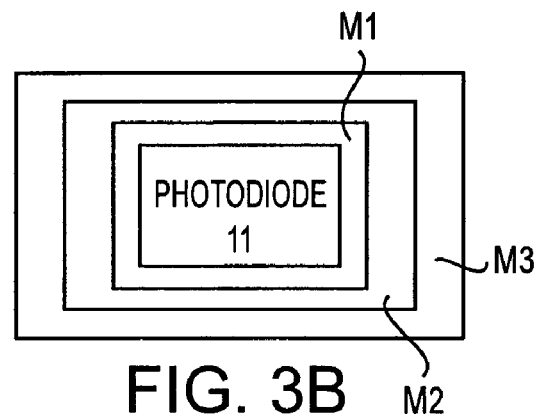
Figure 3C:
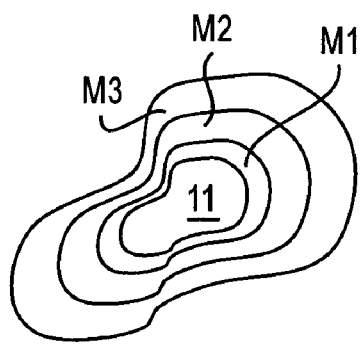
Figure 3D:
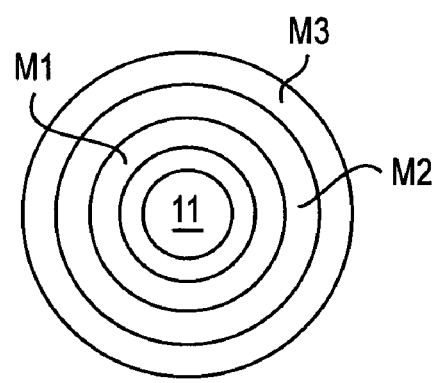
Figure 4:
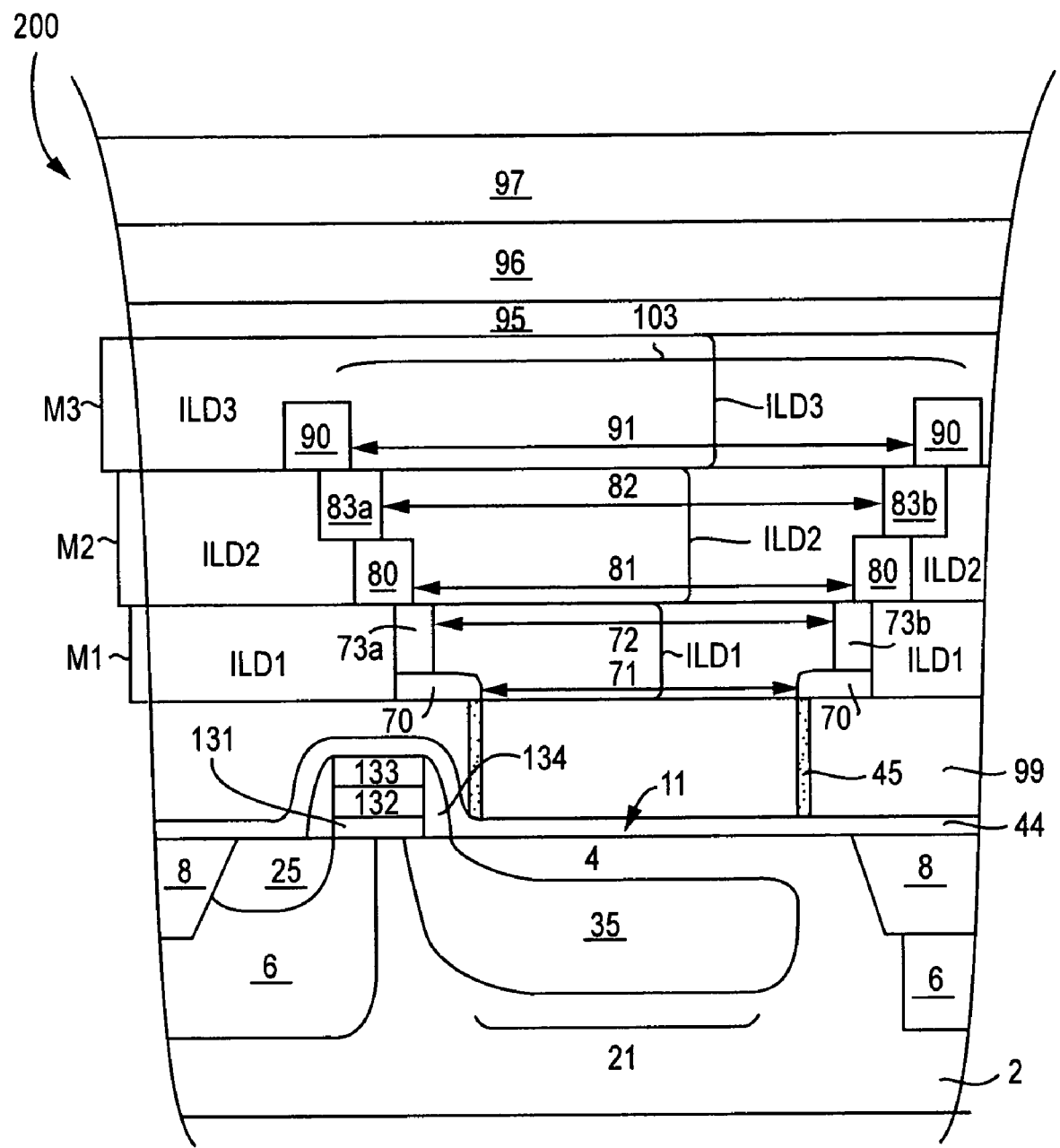
FIG. 4 is a partial cross-sectional view of another embodiment of the pixel cell of FIG. 1 through line 2-2', showing additional conductive interconnect layers and an anti-reflective coating layer.

The invention will now be explained with reference to the accompanying figures wherein like reference numbers are used consistently for like features throughout the drawings. FIGS. 2 and 4 illustrate various exemplary embodiments of a pixel cell 100 (FIG. 2) and pixel cell 200 (FIG. 4) having a respective light tunnel 103 constructed in accordance with the invention.

Now referring to the figures, FIGS. 1-4 illustrate various embodiments of the invention, exemplified in a four transistor (4T) CMOS pixel cell 100 using a photodiode 11 as a photoconversion device. FIGS. 1, 2 and 4 illustrate a multi-layered transfer transistor gate 30 and a reset transistor gate 40 (FIG. 1) formed over substrate 2. For exemplary purposes, substrate 2 is an epitaxial p-type layer over a p-type silicon base layer. However, as noted above, the invention has equal utility with other semiconductor substrates, and, the invention may employ other photoconversion devices instead of a photodiode.

The transfer transistor gate 30 comprises a gate oxide layer 131, a conductive layer 132, and an insulating layer 133 (best seen in FIG. 2). If desired, a silicide layer or a metal layer (not shown) may also be formed in the multi-layered gate stack 30, between the conductive layer 132 and the insulating layer 133. FIGS. 2 and 4 illustrate insulating sidewall spacers 134 formed on the transfer transistor gate 30.

The reset transistor gate 40 comprises a gate oxide layer 141, a conductive layer 142, and an insulating layer 143. If desired, a silicide layer or a metal layer (not shown) may be also formed in the multi-layered gate stack 140, between the conductive layer 142 and the insulating layer 143. The illustrated pixel 100 also includes insulating sidewall spacers 134 formed on the reset transistor gate 40.

The reset transistor gate 40 has an impurity doped source/drain region 23 and shares an impurity doped common source/drain region 25 with the transfer transistor gate 30. The impurity doped common source/drain region 25 is typically known as a floating diffusion region 25. The multi-layered transfer gate 30 transfers charge accumulated in the photodiode 11 to the floating diffusion region 25 when activated. Field oxide regions 8, often referred to as trench isolation regions are formed in substrate 2 separating adjacent pixel cells. In an exemplary embodiment, the regions 8 are shallow trench isolation (STI) regions.

The pixel cell 100 of FIGS. 1 and 2, and pixel cell 200 of FIG. 4, includes a photogenerated charge collection region 21, in a doped portion of the wafer substrate 2, for collecting charges generated by light incident on the pixel cell 100 (FIG. 2) or pixel cell 200 (FIG. 4). This region 21 is formed as a pinned photodiode 11. The photodiode 11 is "pinned" because the potential in the photodiode 11 is pinned to a constant value when the photodiode 11 is fully depleted. It should be understood, however, that either pixel cell 100 or 200 may include a photogate, a photoconductor, or other photon-to-charge converting device, in lieu of a pinned photodiode 11 as the charge collection region 21.

The photodiode 11 is formed in a p-type substrate 2, and comprises a n-type accumulation region 35 and a p-type conductivity layer 4 over the n-type region 35. It should be understood that while FIG. 1 shows the circuitry for a single pixel cell, in practical use there will be a M×N array of pixel cells arranged in rows and columns with the pixel cells of the array accessed using row and column select circuitry, as is known in the art. The pixel cell 100 (FIG. 2) and pixel cell 200 (FIG. 4) can be laterally isolated from other pixel cells of the array by shallow trench isolation regions 8.

The 4T pixel cells 100 or 200, shown in FIG. 1 (and FIGS. 2 and 4) includes a doped p-well 6 in substrate 2 in which the floating diffusion region 25 is found. Each pixel cell 100 or 200 also includes the photodiode 11, transfer gate 30, reset gate 40, source follower gate 50, and row select gate 60. The transfer gate 30 forms part of a transfer transistor for electrically gating the charges accumulated by photodiode 11 to the floating diffusion region 25.

A first conductor 26, at the floating diffusion region 25, is electrically connected with the gate 50 of the source follower transistor through a second conductor 34 (although the conductors, i.e., 26 and 34, are not shown in the exploded view of FIG. 1, they would follow the dotted lines associated therewith to the conductive path 70). The two conductors 26 and 34 are electrically connected by the conductive path 70 in a conductive interconnect layer, e.g., the M1 layer. Sharing the floating diffusion region 25 with the transfer transistor is the reset transistor having gate 40. The reset transistor is connected to a voltage source ($V_{dd}$) through a source/drain region having a conductor 17 for providing a reset voltage to the floating diffusion region 25.

Figure 13:
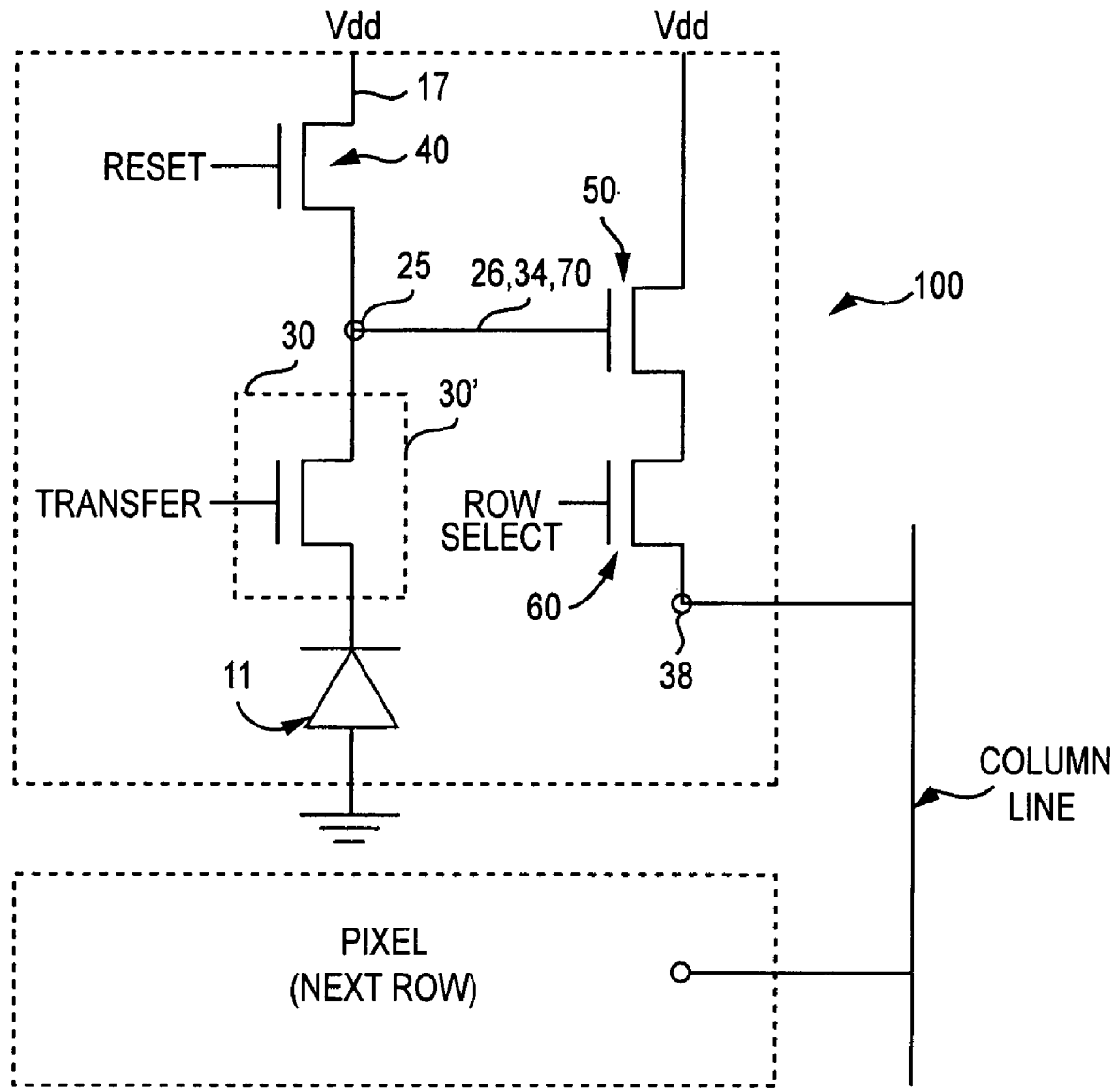
FIG. 13 shows circuit diagram of a 4T pixel like that shown in FIG. 1.

An electrical equivalent circuit for the pixel cell 100 is illustrated in FIG. 13 with a pixel cell, such as pixel cell 100 or 200, being operated as known in the art by RESET, TRANSFER, and ROW SELECT signals. As shown in FIG. 13, the 4T circuit can be converted to a three transistor (3T) circuit by the removal of the portion contained within the dotted box 30', i.e., the transfer transistor, and electrically coupling the photodiode 11 output to the floating diffusion region 25 within the p-well region 6, the floating diffusion region 25 being connected to the gate 50 of the source follower transistor.

As FIG. 2 illustrates and described in relation thereto, a transparent dielectric layer 99 can be provided over the underlying structures of pixel cell 100. The transparent dielectric layer 99 is a conformally-deposited layer that can be planarized to provide a substantially smooth top surface, if desired. The transparent dielectric layer 99 can comprise a transparent material that allows light to pass through to the photodiode 11 such as, e.g., silicon dioxide, BSG, PSG, or BPSG. The transparent dielectric layer 99 is typically planarized and etched to provide contact holes, which are then metallized to provide contacts to floating diffusion region 25 and other areas of pixel cell 100.

An M1 layer is provided over the conformally deposited transparent dielectric layer 99. The M1 layer comprises conductive interconnect patterns 70 and interlevel dielectric layer material 1 ("ILD 1") formed over pixel cell 100. The conductive interconnect patterns 70 are deposited over transparent dielectric layer 99 and patterned to the desired shape. The conductive interconnect patterns 70 form what is known in the art as a metallization level layer. The ILD 1 is formed over the transparent dielectric layer 99, within aperture 71, over conductive interconnect patterns 70, and patterned to the desired shape. The ILD 1 layer is known in the art as a "Via level" layer and should have similar light transmitting and insulating properties as the transparent dielectric layer 99. However, the ILD 1 layer can comprise similar or different materials than transparent dielectric layer 99, so long as they have similar light transmitting and insulating properties.

Any metal and ILD 1 can be used that is well-known in the art to comprise the M1 layer. The M1 layer may be connected by electrical contacts to the underlying circuitry provided in openings 48 through the various layers comprising the M1 layer through any well-known techniques in the art. As FIG. 2 illustrates, conductive interconnect patterns 70 are formed having an aperture 71. In one exemplary embodiment, aperture 71 in the M1 layer is approximately the same width as the width of the photodiode 11. In another embodiment, aperture 71 is wider than the width of the photodiode 11. In still yet another embodiment, aperture 71 is narrower than the width of the photodiode 11. Aperture 71 is the distance separating conductive interconnect patterns 70.

As FIG. 2 further illustrates, ILD 1 is formed with vertical metallization interconnect lines 73a and 73b. The vertical metallization interconnect lines 73a, 73b are distanced apart from each other by aperture 72. Vertical metallization interconnect lines 73a, 73b electrically connect conductive interconnect patterns 70 with subsequently deposited conductive interconnect patterns, i.e., conductive interconnect pattern 80. In one exemplary embodiment, aperture 72 in the M1 layer is approximately the same width as the width of aperture 71. In another embodiment, aperture 72 is wider than the width of aperture 71. In still yet another embodiment, aperture 72 is narrower than the width of aperture 71.

It should be appreciated that the M1 layer can be formed with apertures 71 and 72 that focus and direct light onto pixel cell 100 with the assistance of conductive interconnect patterns 70 and vertical metallization interconnect lines 73a, 73b, i.e., directly onto the photodiode 11. The presence of conductive interconnect patterns 70 and vertical metallization interconnect lines 73a, 73b form a light tunnel structure that directs light onto photodiode 11. In other words, the lateral profile of apertures 71 and 72 can be manipulated depending upon the desired characteristics of the desired light tunnel 103. The ILD 1 material is present in apertures 71 and 72.

Apertures 71 and 72 can be modified to have any shape and size depending on the amount of incident light desired to impinge on photodiode 11. In yet another embodiment, apertures 71 and 72 can be formed to have the exact same top down layout shape as photodiode 11. For example, in FIG. 3A, if the photodiode 11 has a relatively square shape, apertures 71 and 72 can be formed to have a square shape. If the photodiode 11 has a rectangular shape (FIG. 3B), an irregular shape (FIG. 3C), a circular shape (FIG. 3D), or any other myriad of shapes, apertures 71 and 72 can be formed to have an opening that is substantially the same shape as the photodiode 11.

Referring back to FIG. 2, an M2 layer is formed over the M1 layer. Intervening layers can be formed between the M1 layer and M2 layer, if desired. The M2 layer comprises conductive interconnect patterns 80 and interlevel dielectric layer material 2 ("ILD 2") formed over pixel cell 100. The M2 layer may be connected by electrical contacts to the underlying circuitry provided in openings 48 through the various layers comprising the M1 and M2 layers.

The conductive interconnect patterns 80 form what is known in the art as a metallization level layer. The ILD 2 forms what is known in the art as a "Via level" layer and should have similar light transmitting and insulating properties as ILD 1 and the transparent dielectric layer 99. However, ILD 2 can comprise similar or different materials than ILD 1 and transparent dielectric layer 99, so long as they have similar light transmitting and insulating properties. Similarly, the metal comprising the M2 layer can be the same or different than the metal comprising the M1 layer.

Any metal and ILD 2 can be used, that is well-known in the art, to comprise the M2 layer. As FIG. 2 illustrates, conductive interconnect patterns 80 are formed having an aperture 81 and the ILD 2 is formed having an aperture 82. Aperture 81 is the distance between the conductive interconnect patterns 80. Aperture 82 is the distance between the vertical metallization interconnect lines 83a, 83b. In one exemplary embodiment, aperture 82 in the M2 layer is approximately the same width as the width of aperture 81. Aperture 81 can be formed the same width, smaller, or wider than apertures 71 and 72. In another embodiment, aperture 82 is wider than the width of aperture 81. In still yet another embodiment, aperture 82 is narrower than the width of aperture 81.

In one exemplary embodiment, apertures 81 and 82 are approximately wider than the width of apertures 71 and 72. It should also be appreciated that apertures 81 and 82 can be made the same width or smaller than apertures 71 and 72.

It should be further appreciated that when used in conjunction, the M1 and M2 layers, comprising apertures 71, 72, 81, and 82, can focus and direct light incident on pixel cell 100, directly onto the photodiode 11. The conductive interconnect patterns 70, 80, and vertical metallization interconnect lines 73*a*, 73*b*, 83*a*, and 83*b* form a light tunnel structure. The light tunnel structure assists in focusing light onto photodiode 11. Consequently, the lateral profile of apertures 71, 72, 81, and 82 can be manipulated depending upon the desired characteristics of the desired light tunnel 103.

Accordingly, apertures 71, 72, 81, and 82 can be modified to have any shape and size depending on the amount of incident light desired to impinge on photodiode 11 as FIGS. 3A-3D illustrate. It is important to note, that it is preferred that conductive interconnect patterns 70 and ILD 1 are wider, i.e., both layers having narrower apertures 71 and 72, than conductive interconnect patterns 80 and ILD 2, i.e., both having wider apertures 81 and 82 than apertures 71 and 72, to create a step-like, or ladder-like light tunnel structure 103 to focus light onto photodiode 11.

Still referring to FIG. 2, an M3 layer may be formed over the M2 and M1 layers. Intervening layers can be formed between the M3 layer and M2 layer, if desired. The M3 layer comprises conductive interconnect patterns 90 and interlevel dielectric layer material 3 ("ILD 3") formed over pixel cell 100. The conductive interconnect patterns 90 form what is known in the art as a metallization level layer. The ILD 3 layer forms what is known in the art as a "Via level" layer and should have similar light transmitting and insulating properties as ILD 1, ILD 2, and the transparent dielectric layer 99. However, the ILD 3 layer can comprise similar or different materials than ILD 1, ILD 2, and transparent dielectric layer 99, so long as they all have similar light transmitting and insulating properties. Similarly, the metal comprising the M3 layer can be the same or different than the metal comprising the M1 and M2 layers.

Any metal and ILD 3 can be used, that is well-known in the art, to comprise the M3 layer. The M3 layer may be connected by electrical contacts to the underlying circuitry provided in openings 48 through the various layers comprising the M1 and M2 layers. As FIG. 2 illustrates, conductive interconnect patterns 90 are formed having an aperture 91. Aperture 91 can be approximately the same width as aperture 81 or 82. In another embodiment, aperture 91 is wider than the width of aperture 81. In still yet another embodiment, aperture 91 can be formed narrower than the width of apertures 81 and 82. In one exemplary embodiment, aperture 91 is wider than the width of apertures 71, 72, 81, and 82.

It should be further appreciated that when used in conjunction, the M1, M2 and M3 layers, comprising apertures 71, 72, 81, 82, and 91 can focus and direct light incident on pixel cell 100, directly onto the photodiode 11. The conductive interconnect patterns 70, 80, and 90, and vertical metallization interconnect lines 73*a*, 73*b*, 83*a*, and 83*b* form a light tunnel structure. The light tunnel structure assists in focusing light onto photodiode 11. Consequently, the lateral profile of apertures 71, 72, 81, 82, and 91 92 can be manipulated depending upon the desired characteristics of the desired light tunnel 103.

Accordingly, apertures 71, 72, 81, 82, and 91 can be modified to have any shape and size depending on the amount of incident light desired to impinge on photodiode 11 as FIGS. 3A-3D illustrate. For example, the shape of the light tunnel 103 structure in FIG. 2, can be gradually morphed or changed into a different shape with each subsequent layer, e.g., M1, M2, and M3 layers, to end up with a light tunnel 103 having a shape that substantially matches or overlaps the photodiode 11. It should also be appreciated that the light tunnel 103 can comprise a single layer such as only the M1 layer, or two layers, such as the M2 and M1 layers, or a plurality of layers such as the M1, M2, and M3 layers.

It is important to note, that it is preferred that the apertures 71 and 72 of conductive interconnect patterns 70 and ILD 1 are wider than the apertures 81 and 82 of conductive interconnect patterns 80 and ILD 2, and the aperture 91 of conductive interconnect patterns 90, to create a step-like or ladder-like light tunnel 103 that focuses light onto photodiode 11. Arrows 101 indicate how light can be focused and guided by the M1, M2, and M3 layers comprising the light tunnel 103. At this point, the light tunnel 103 in FIG. 2 is complete. Additional fabrication steps can be carried out such as a nitride passivation layer 95 formed over the M3 layer with a color filter array 96 and micro-lens 97 formed over thereon.

In FIG. 2, a gap ("$X_{gap}$") is present between the M1 layer and the surface of photodiode 11. However, in another embodiment illustrated in FIG. 4, there is no $X_{gap}$. The $X_{gap}$ present in FIG. 2, in some instances depending on how the light tunnel is formed, may allow light to escape into surrounding periphery structures since there is nothing to constrict the light for disbursing upon hitting the surface of photodiode 11. To address this concern, the pixel cell 200 of FIG. 4 is provided with a structure that can prevent light from escaping into surrounding peripheral structures.

Referring now to FIG. 4, an optional anti-reflective coating layer 44 (FIGS. 1 and 4) can be provided over the pixel cell 200 circuitry. The anti-reflective coating layer 44 can comprise any materials that are well-known in the art. The optional anti-reflective coating layer 44 can be a conformally-deposited layer over the pixel cell 200. The anti-reflective coating layer 44 can then be planarized, if desired.

As shown in FIG. 4 and described in relation thereto, a transparent dielectric layer 99 can be formed over the anti-reflective coating layer 44 ("ARC layer 44") and the underlying pixel cell 100. The transparent dielectric layer 99 is a conformally-deposited layer formed over the anti-reflective layer 44. In this embodiment, the lateral confinement of light incident on pixel cell 200 is enhanced with the addition of the anti-reflective coating layer 44 in combination with metal contact rings 45. The ARC layer 44 should be patterned so as to not block contact areas. Thus, additional masks are not needed to open both contacts and the light tunnel 103 features at the same time. If desired, a separate mask and etch to form light tunnel 103 can also be employed.

ARC layer 44 and metal contact rings 45 prevent light from escaping once it nears photodiode 11 as may occur in FIG. 2 depending on the light tunnel structure 103. In addition, the metal contact rings 45 are connected at least in part to conductive interconnect pattern 70. The metal contact rings 45 do not go through ARC layer 44. The metal contact rings 45 can be formed to have a width that is substantially the same width as photodiode 11. The metal contact rings can also be formed to have a larger or smaller width than photodiode 11. After formation of the metal contact rings 45 and transparent dielectric 99, the formation and structure of the subsequent M1, M2, and M3 layers is analogous to the FIG. 2 embodiment.

In the structural embodiments illustrated in FIGS. 1-4, the transparent dielectric layer 99 should be from about 0.5 to about 0.8 micron's thick. The M1, M2, and M3 layers should be from about 0.1 to about 1 micron's thick. ARC layer 44 should be approximately 0.05 microns thick.

It should also be appreciated that additional openings 48 are provided in the anti-reflective coating layer 44 and dielectric layer 99 to allow various circuitry contacts to be in electrical communication between overlying conductive interconnect layers 70, 80, and 90 such as M1, M2, M3, etc., and underlying pixel circuitry, e.g., 30, 40, 50, and 60.

By structuring each of the metal and Via level layers, e.g., the M1, M2 and M3 layers, properly, a light tunnel 103 with a 'stair-case,' 'step-like,' 'funnel-like,' or 'ladder-like,' shape can be integrated into pixel cell 100 or 200, without the complexity of additional processing steps. The metal width's used for each conductive interconnect pattern 70, 80, and 90, would be compatible with current ground rules (e.g., approximately 0.1-0.3 μm) and provide enough reflectivity to essentially confine the light inside the funnel-like shape of light tunnel 103, formed by the varying metallization and via level layers, e.g., the M1, M2 and M3 layers.

The light tunnel 103 structure is particularly useful in smaller pixel cell sizes such as those pixel cells which are less than 2.8 μm, and even more useful in pixel cells which are less than 2.0 μm. The lateral steps of the metallization layers would be well below the wavelength of visible light. Thus, avoiding reflection and refraction losses currently associated with pixel cells not employing light tunnel 103. Accordingly, crosstalk is reduced because pixel cell 100 and pixel cell 200 confines light rather than reflects or refracts it.

Further, the top metallization layer, in this case, the M3 layer of FIGS. 2 and 4, would not be used for wiring to prevent refraction and reflection. This would maximize light collection. The top metallization layer, e.g., the conductive interconnect pattern 90, has less surface area than conductive interconnect patterns 80 and 70. Thus, there is less area for light to reflect from. This enhances the pixel cell's ability to efficiently use light. Light would be focused through the top metal aperture 91. The additional assistance of ILD 1, ILD 2, and ILD 3 having vertical metallization interconnects 73a, 73b, 83a, and 83b, also helps to direct light down to photodiode 11 when used with conductive interconnect patterns 70, 80, and 90. Although not illustrated, the M3 layer can be formed with vertical metallization interconnects, if desired.

The light capturing ability of the light tunnel 103 structure can be enhanced by employing a micro-lens 97 with a focal length that maximizes the angular acceptance range of the pixel cell while keeping cross-talk at the bottom of the light tunnel 103 at a minimum. Accordingly, if the photodiode 11 at the bottom of the light tunnel 103 has a non-square or even a non-linear shape, the light tunnel 103 can be gradually adapted, i.e., morphed, to that shape by configuring each respective metallization and via layer, i.e., M1, M2, and M3 layers to the desired shape (FIGS. 3A-3D).

In another embodiment, the edges of the conductive interconnect patterns 70, 80, and 90, and ILD 1, ILD 2, and ILD 3 have rounded edges to assist in guiding light incident on pixel cell 100. In addition, the rounded edges reduce the possibility of reflection or refraction of light incident on pixel cell 100. It is also possible, with the various structural embodiments of this invention, to entirely avoid the use of micro-lenses since the funnel-like light tunnel 103 structure, focuses light as a micro-lens does. It should be appreciated that although only three metallization and via level layers, e.g., M1, M2 and M3 are illustrated, more than or less than the metallization and via level layers illustrated can be used. For example, n*(M1–Mx) can be used (any number times the number of metallization layers to via level layers).

A method of forming the pixel cell 100 of FIGS. 1 and 2 and pixel cell 200 of FIG. 4 is now described with reference to FIGS. 5-12.

Figure 5:
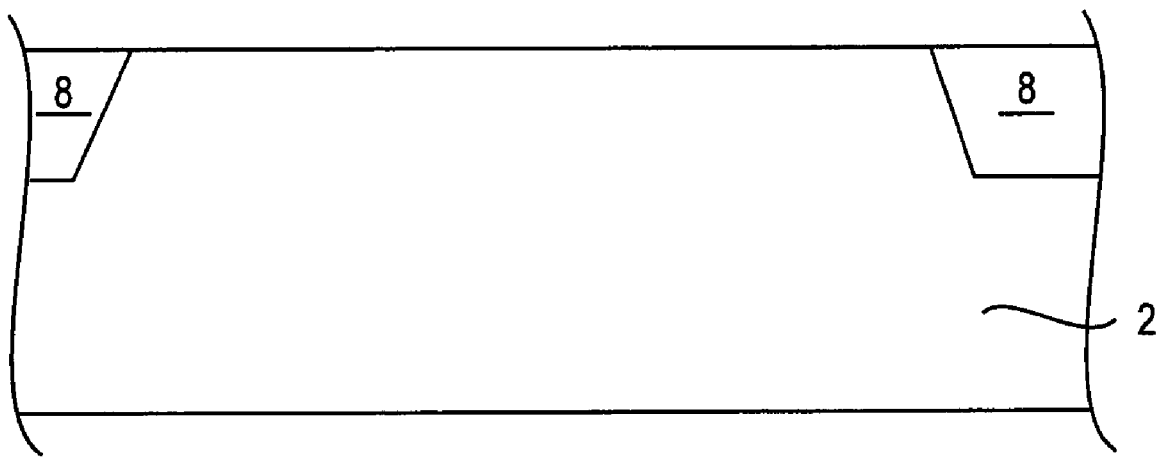
FIG. 5 shows a stage of fabrication of a pixel in accordance with one exemplary embodiment of the present invention.

FIG. 5 shows a preliminary stage of processing. As mentioned above in discussing FIGS. 1 and 2, the pixel cell 100, and pixel cell 200 of FIG. 4, is isolated within the substrate 2 by isolation regions 8, which are preferably STI (shallow trench isolation) regions, but may also be formed by LOCOS processing. The STI isolation regions 8 can be formed by using a photoresist mask, patterning, and etching to leave trenches where the isolation regions 8 are desired. The photoresist is removed. A layer of dielectric material (e.g., silicon dioxide, silicon nitride, oxide-nitride, nitride-oxide, or oxide-nitride-oxide, etc.) is formed within the trenches by CVD, LPCVD, HDP, or other suitable means. After filling the trenches with the dielectric material, the wafer is planarized, for example by CMP or RIE dry etching processes, and the isolation regions 8 are complete as shown in FIG. 5 and surround the pixel cell 100.

Figure 6:
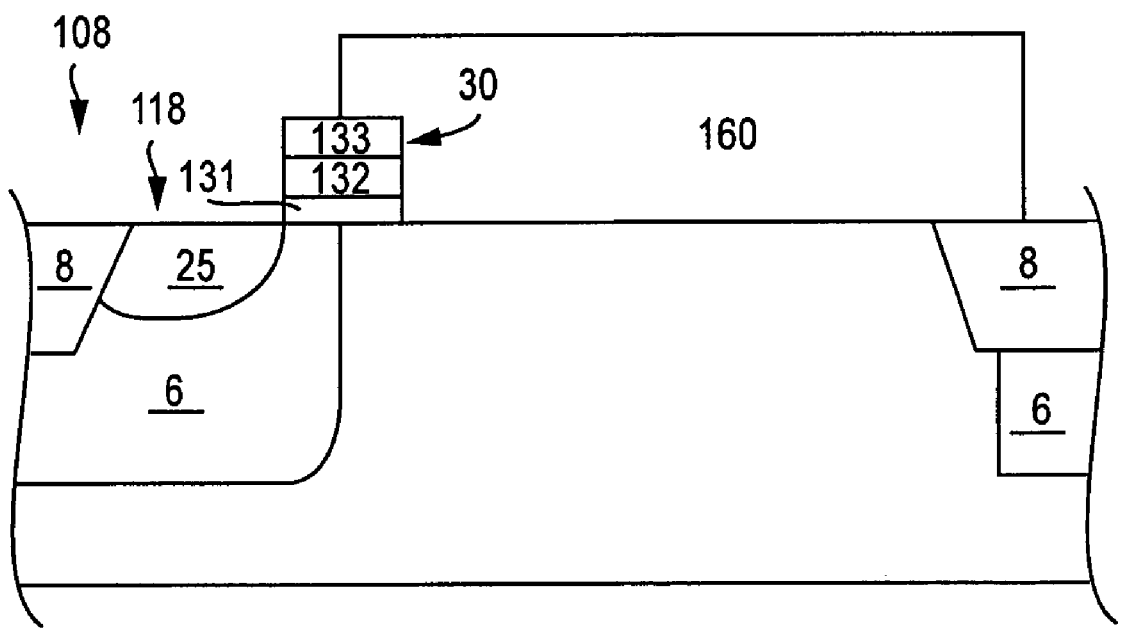
FIG. 6 shows a stage of fabrication subsequent to that illustrated in FIG. 5.

Next, as shown in FIG. 6, transistor gates are formed, including the transfer gate 30 shown in FIG. 1, FIG. 2, and FIG. 4. Standard MOS gates are formed by forming a gate oxide layer 131 (e.g., silicon oxide) over the substrate 2, then forming a doped polysilicon layer 132 over the gate oxide layer 131 (the polysilicon layer can be doped in situ or subsequently implanted with a dopant), and then forming an insulative cap layer 133 (e.g., oxide or nitride). As indicated above, an optional silicide layer can be formed over layer 132, if desired (not illustrated).

After forming the gate stacks, e.g., transfer gate 30, a dopant implant 108 is performed in the substrate 2 to form a p-type region 6 beneath a portion of the pixel cell 100 and 200. A photoresist mask 160 prevents the implant 108 from doping areas of the pixel cell where photodiode 11 will subsequently be formed. As an alternative, the p-type region 6 may be formed by a blanket implant. It should be noted, however, that the dopant conductivity types utilized throughout processing can easily be reversed to form a PMOS type pixel cell, as opposed to an NMOS pixel cell.

After forming the p-type region 6, another implant 118 is used to form a floating diffusion region 25 adjacent to the transistor gate stack 30, as is known in the art (source/drain regions 23 for other transistors (not shown) can be formed simultaneously). The floating diffusion region 25, acts as a source/drain region for the transfer transistor gate 30.

Figure 7:
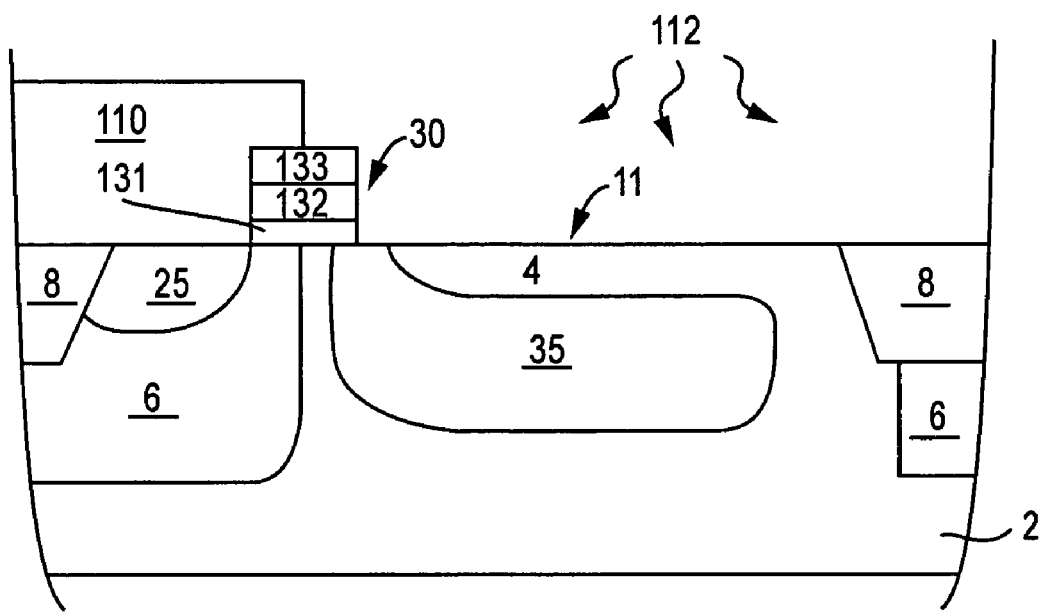
FIG. 7 shows a stage of fabrication subsequent to that illustrated in FIG. 6.

Referring now to FIG. 7, the photodiode 11 comprises a p-n-p structure made of the underlying p-type substrate 2, a n-type region 35 within the p-type region 6, and a p-type layer 4 above the n-type region 35. FIG. 7 shows the substrate 2 being masked with a patterned photoresist 110 and another ion implantation 112 of a second conductivity type, here n-type, being performed. This forms n-type region 35 in the pixel cells 100 and 200 active areas, and below the transfer gate 30. Angled implants 112 can also be utilized to form n-type region 35 to achieve certain spatial characteristics of photodiode 11.

Figure 8:
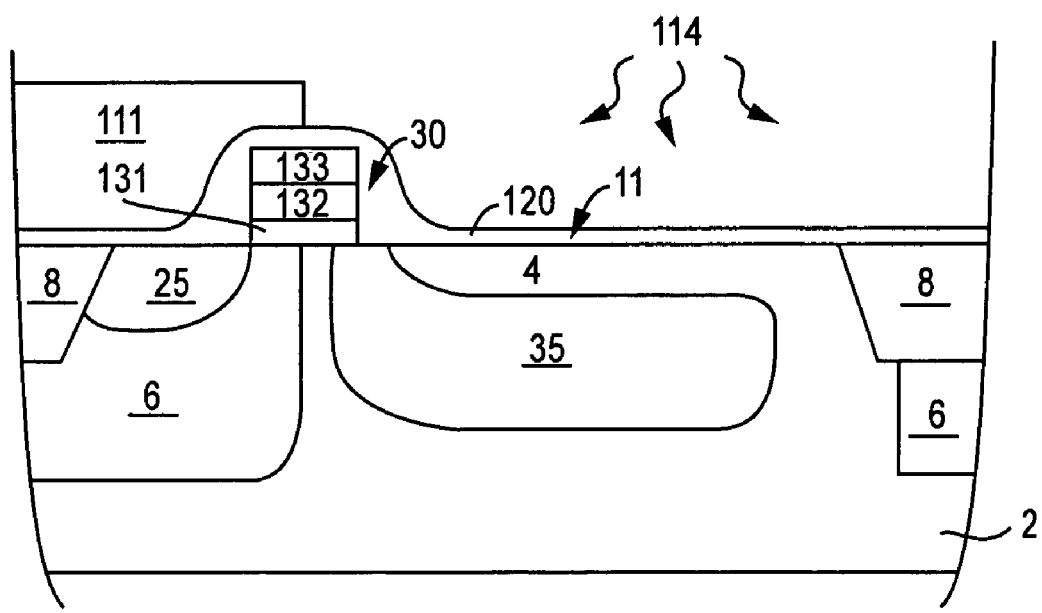
FIG. 8 shows a stage of fabrication subsequent to that illustrated in FIG. 7.

As shown in FIG. 8, after removing the photoresist 110, an insulating layer 120, which forms sidewall spacers 134 is formed over the transistor gate 30 (this same layer 120 can form sidewall spacers for other transistor gates). Another mask of photoresist 111 is formed partially over the transistor gate 30 and a dopant implant 114 is performed to form a top p-type layer 4 of the photodiode 11. Optionally, an angled implant for implant 114 may be used as well. The photodiode 11 is termed a "pinned" photodiode 11 because the potential in the photodiode 11 is pinned to a constant value when it is fully depleted.

Figure 9A:
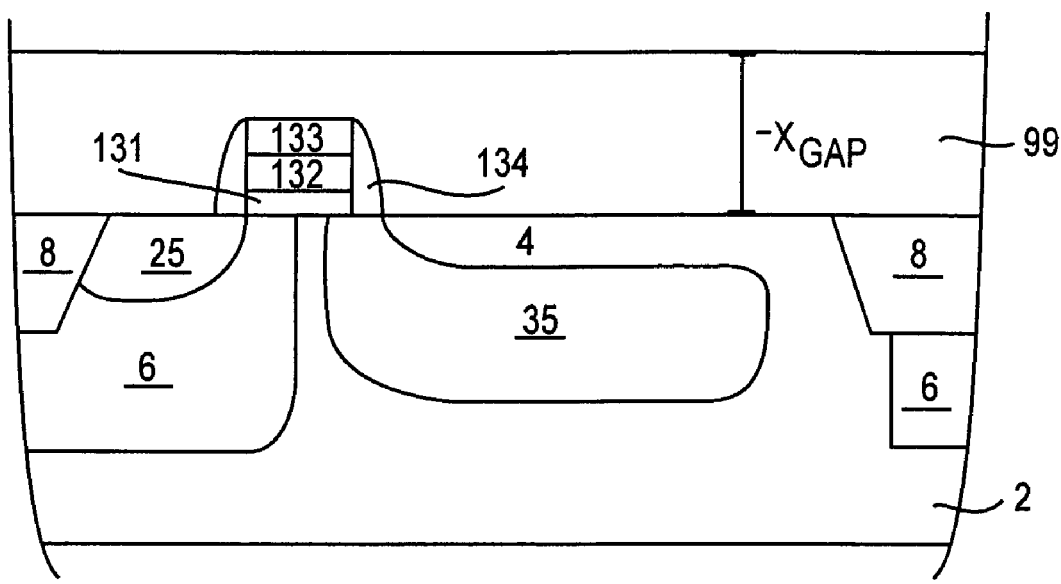
FIG. 9a shows a stage of fabrication subsequent to that illustrated in FIG. 7, for one embodiment of the present invention.

In forming the embodiment of pixel cell 100 of FIG. 2, reference is now made to FIG. 9a. In FIG. 9a, a transparent dielectric layer 99 is deposited over the pixel cell 100 circuitry, including the transfer gate 30. This transparent dielectric layer 99 should be optically transparent so as not to impede light from reaching the photodiode 11. The transparent dielectric layer 99 can comprise, e.g., silicon oxides or nitrides, glasses, or polymeric materials, and can be deposited by evaporative techniques, CVD, PECVD, sputtering, or other techniques known in the art. The dielectric layer 99 may be planarized by various techniques, such as CMP or RIE etching. Alternatively, if a conformal dielectric layer is desired, the planarization step can be excluded.

Figure 9B:
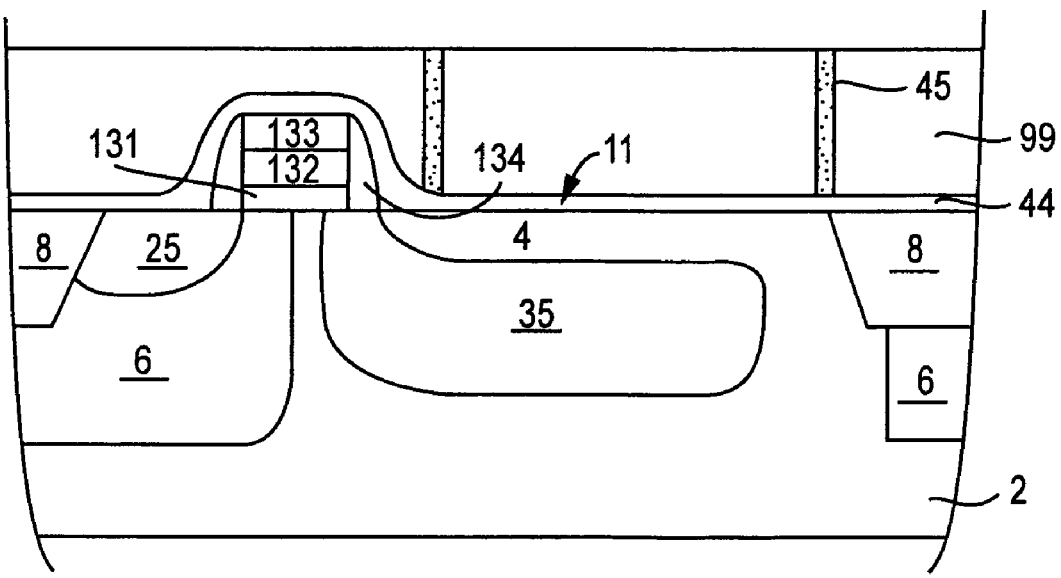
FIG. 9b shows a stage of fabrication subsequent to that illustrated in FIG. 7, for another embodiment of the present invention.

In forming the embodiment of pixel cell 200, reference is now made to FIG. 9b. In FIG. 9b, the anti-reflective coating layer 44 is conformally formed over the pixel cell's 200 circuitry. The anti-reflective coating layer 44 can be a conformal layer or planarized. The anti-reflective coating layer 44 should be approximately 0.05 microns thick. The anti-reflective coating layer 44 can comprise any material well-known in the art. The anti-reflective coating layer 44 is positioned over photodiode 11. At this point, a transparent dielectric layer 99 is formed over the anti-reflective coating layer 44.

Still referring to FIG. 9b, a photoresist and mask are then applied (not illustrated) to etch portions of transparent dielectric layer 99 and fill the etched portions with a conductive material to form metal contact rings 45. The anti-reflective coating layer 44 is not etched. The metal contact rings 45 are used to enhance and further direct light incident upon photodiode 11. This mitigates the problem of cross-talk near the surface of photodiode 11. The metal contact rings 45 can be formed to have substantially the same width as photodiode 11, smaller, or larger, if desired. The metal contact rings 45 serve to prevent light from reflecting or refracting from surrounding periphery structures, and, to prevent the light directed to photodiode 11 from escaping.

Figure 10:
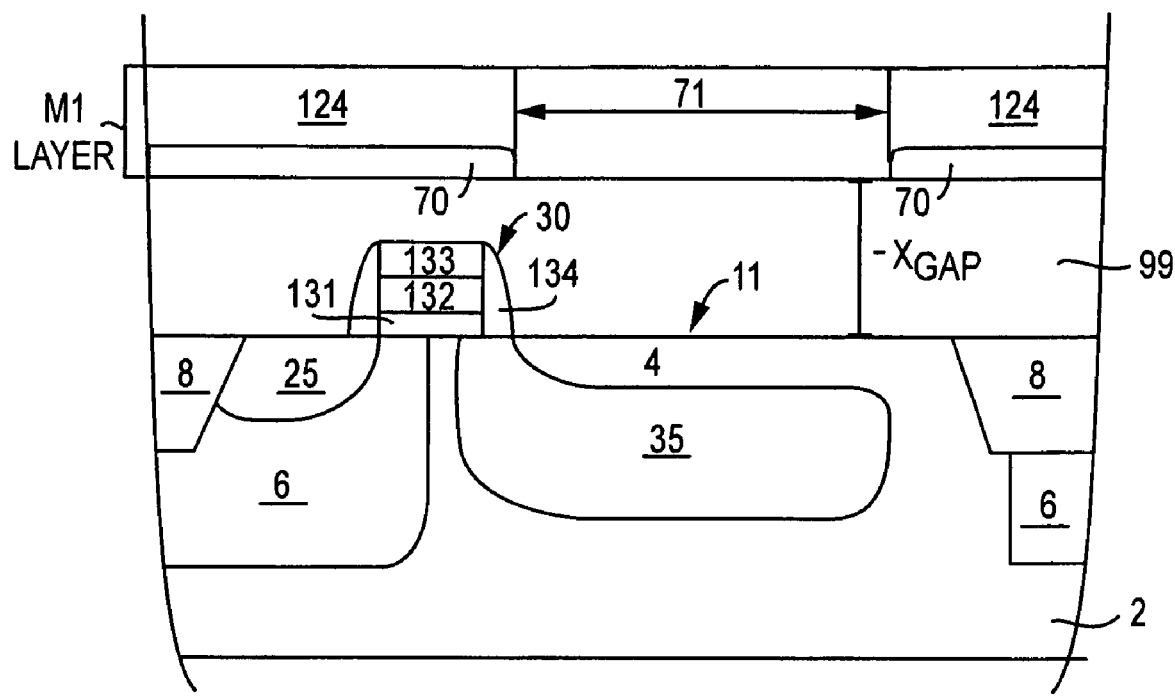

FIG. 9b is different from FIG. 9a, since it employs metal contact rings 45 and an anti-reflective coating layer 44. This is different from the structural embodiment of FIG. 9a, in which a $X_{gap}$ is present between the transparent dielectric layer 99 and a subsequently deposited metallization layer (FIG. 10). As FIG. 9b illustrates, there is no gap present since the metal contact rings 45 would connect with a subsequently deposited metallization layer, i.e., interconnect pattern 70 of FIG. 10.

Figure 11:
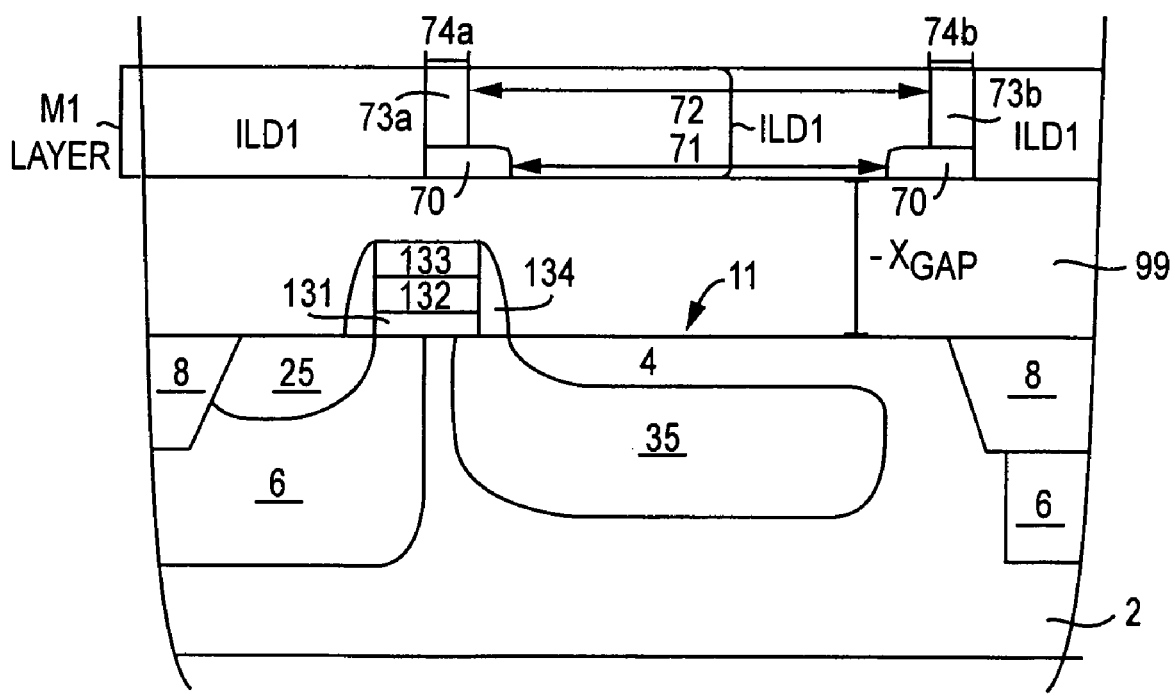
FIG. 11 shows a stage of fabrication of a circuit subsequent to that shown in FIG. 10.
Figure 12:
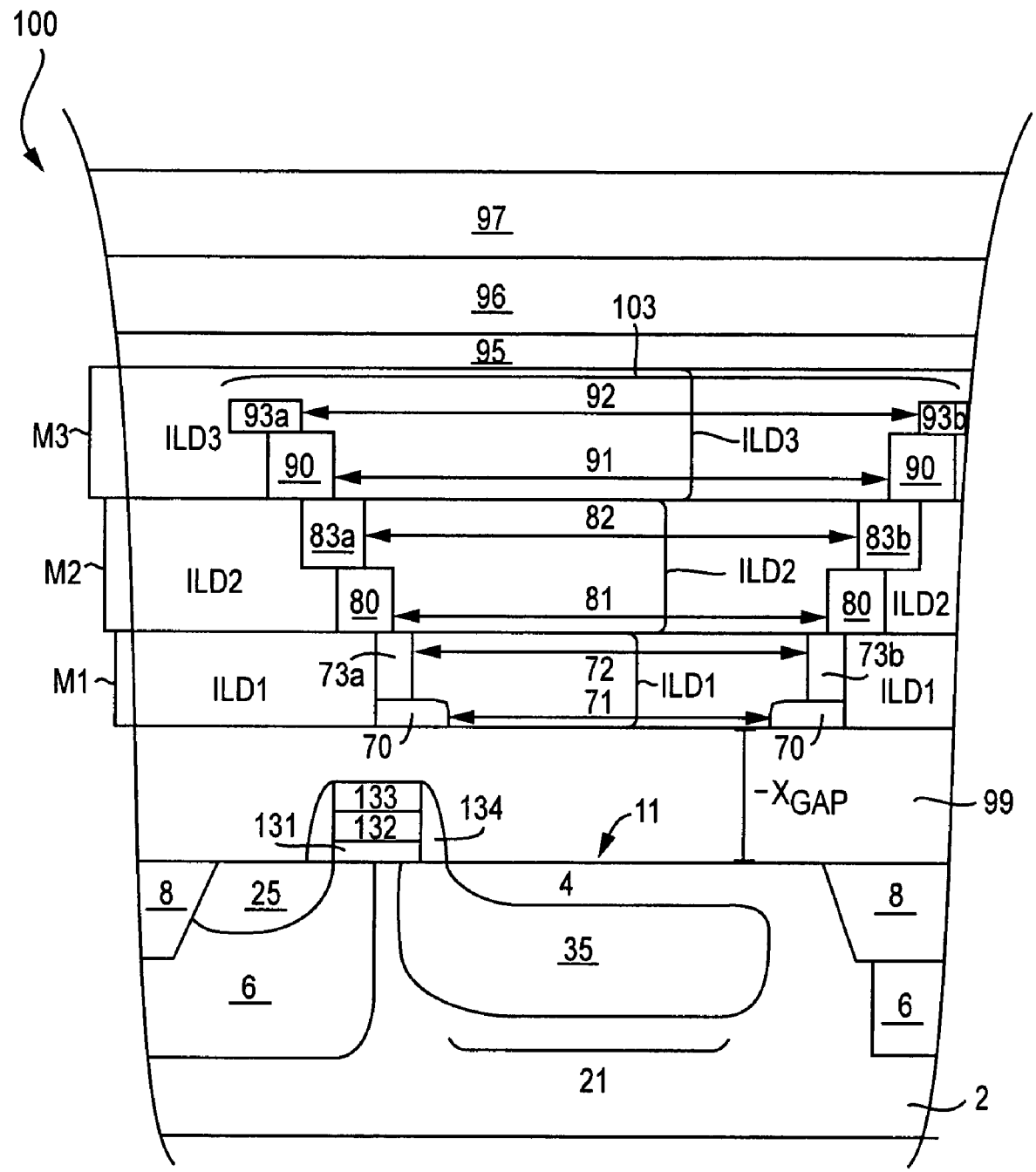
FIG. 12 shows a stage of fabrication of a circuit subsequent to that shown in FIG. 11.

As such, from this point on, pixel cell 100 of FIG. 9a and pixel cell 200 of FIG. 9b, can both be fabricated according to the subsequent steps provided in FIGS. 10-12. For purposes of a simplified description, reference will now be made to completing the formation of pixel cell 100, subsequent to the method disclosed in FIG. 9a, and light tunnel 103.

Referring now to FIG. 10, an M1 layer comprising conductive interconnect patterns 70 and an ILD 1 layer are deposited over the first dielectric layer 99. The conductive interconnect patterns 70 are conformally deposited over pixel cell 100. A patterned photoresist 124 is formed over conductive interconnect patterns 70 and subsequently etched to form an aperture 71. Aperture 71 is the distance between the conductive interconnect patterns 70. Depending on the size and shape of the photodiode for pixel cell 100, the patterned photoresist 124 will be used to form the desired shape and aperture 71 of conductive interconnect patterns 70. Photoresist 124 is then removed.

Now referring to FIG. 11, an ILD 1 layer is conformally deposited and formed over the conductive interconnect patterns 70 and over the structures of pixel cell 100. The ILD 1 layer can be the same or similar in composition, light transmission, and dielectric properties as the transparent dielectric layer 99. ILD 1 can also be deposited in a similar fashion. A second patterned photoresist is formed over the ILD 1 and the second patterned photoresist is used to form openings 74a and 74b within ILD 1. A conductive metal is then deposited within openings 74a and 74b to form vertical conductive interconnects 73a and 73b. The vertical conductive interconnects 73a and 73b electrically connect conductive interconnect patterns 70 with subsequently deposited metallization layers, i.e., conductive interconnect patterns 80 and 90 (FIG. 2).

Aperture 72 is the distance separating the two vertical conductive interconnects 73a and 73b from each other. Depending on the size and shape of the photodiode 11 and aperture 71 for pixel cell 100, the second patterned photoresist will be used to form the desired shape and aperture 72 of ILD 1. The second photoresist is removed. Conductive interconnect patterns 70 and vertical conductive interconnects 73a and 73b can comprise any conductive materials well-known in the art. The ILD 1 can then be planarized by any techniques such CMP or RIE etching techniques.

Together, conductive interconnect patterns 70, vertical conductive interconnects 73a, 73b, apertures 71, 72, and ILD 1 form the M1 layer as illustrated in FIG. 11. In one exemplary embodiment, apertures 71 and 72 are approximately the same width as the width of the photodiode 11. In another embodiment, apertures 71 and 72 are wider than the width of the photodiode 11. In still yet another embodiment, apertures 71 and 72 are narrower than the width of the photodiode 11. Moreover, it should be appreciated that aperture 72 can have a width that is substantially similar, wider, or narrower than aperture 71.

Conductors to the pixel cell 100 circuitry's active areas are formed as is well-known in the art. One such conductor would be formed to the floating diffusion region 25. The floating diffusion region 25 is electrically connected with the source follower gate 50 through standard metallization steps, e.g., forming a conductor to the floating diffusion region 25 and a conductor to the source follower gate 50, and forming conductive interconnects 70 there-between.

Additional processing can follow, such as the formation of the M2 and M3 layers comprising conductive interconnect patterns 80 and 90 and ILD 2 and ILD 3, respectively, as illustrated in FIG. 12. The formation of the M2 and M3 layers proceed in an analogous fashion as described in the formation of the M1 layer. The M2 and M3 layers are subsequently formed over the M1 layer. Between each M1, M2, and M3 layer, additional intervening layers can be provided, if desired.

For example, the conductive interconnect patterns, i.e., conductive interconnect patterns 80 and 90, are conformally deposited over pixel cell 100. A patterned photoresist is formed over the conductive interconnect patterns and subsequently etched thereby separating the conductive interconnect patterns with an aperture, such as apertures 81 or 91 (FIG. 2). Depending on the size and shape of photodiode 11 for pixel cell 100, the patterned photoresist will be used to form the desired shape and apertures 71, 81, and 91 for conductive interconnect patterns 70, 80, and 90. The photoresist is then removed after formation of the aperture, i.e., apertures 71, 81, and 91.

Then, the ILD 2 or ILD 3 layer is conformally deposited and formed over the conductive interconnect patterns and over the structures of pixel cell 100, e.g., gate 30. The ILD 2 and ILD 3 layers can be the same or similar in composition, light transmission, and dielectric properties, to the ILD 1 layer or each other, and to the transparent dielectric layer 99. The ILD 2 and ILD 3 layers can be deposited in a similar fashion. A subsequent patterned photoresist is formed over the conductive interconnect patterns and the ILD 2 or ILD 3 layer and is subsequently etched to form openings in which vertical conductive interconnects are formed, i.e., 83a, and 83b (FIG. 2). The vertical conductive interconnects 83a and 83b are separated in distance from each other by aperture 82, and the vertical conductive interconnects 93a and 93b are separated in distance from each other by aperture 92 (FIG. 12). Depending on the size and shape of photodiode 11 for pixel cell 100, the patterned photoresist will be used to form the desired shape and apertures 72, 82, and 92 for ILD 1, ILD 2, and ILD 3. The patterned photoresist is then removed after formation of the aperture, i.e., apertures 72, 82, and 92. Conductive interconnect patterns 80 and 90 can comprise any conductive materials well-known in the art. The ILD 2 and ILD 3 layers can then be planarized by any techniques such CMP or RIE etching techniques.

Together, conductive interconnect patterns 80, vertical conductive interconnects 83a, 83b, apertures 81, 82, and ILD 2 form the M2 layer as illustrated in FIG. 12. Together, conductive interconnect patterns 90, vertical conductive interconnects 93a, 93b, apertures 91, 92, and ILD 3 form the M3 layer as illustrated in FIG. 12. The combination of the M1, M2, and M3 layers, form a light tunnel structure 103 for pixel cell 100. Specifically, the presence and combination of conductive interconnect patterns 70, 80, 90, and vertical conductive interconnects 73a, 73b, 83a, 83b, 93a, and 93b help to guide light onto photodiode 11 by forming light tunnel structure 103.

It is preferred that the conductive interconnect patterns 70 are formed wider, i.e., having a smaller aperture 71, than conductive interconnect patterns 80 and ILD 1, i.e., having a wider aperture 81 and 72, respectively, than aperture 71, to create a step-like, or ladder-like light tunnel 103 structure to focus light onto photodiode 11. Similarly, it is preferred that the conductive interconnect patterns 80 are formed wider, i.e., having a smaller aperture 81, than conductive interconnect patterns 90 and ILD 2, i.e., having a wider aperture 81 than apertures 71 and 72, to create a light tunnel 103 that focuses light onto photodiode 11. The M2 and M3 layers may be connected by electrical contacts to the underlying circuitry provided in openings through the various layers comprising the M1, M2 and M3 layers.

As indicated above, light tunnel 103 can be modified to have any shape and size depending on the amount of incident light desired to impinge on photodiode 11. For example, in FIG. 3A, if the photodiode 11 has a relatively square shape, the apertures 71, 72, 81, 82, 91 and 92 can be formed to have a decreasing square shape. If the photodiode 11 has a rectangular shape (FIG. 3B), an irregular shape (FIG. 3C), a circular shape (FIG. 3D), or any other myriad of shapes, the apertures 71, 72, 81, 82, 91 and 92 comprising the light tunnel 103, can be formed to have an opening that is substantially the same shape as the photodiode 11, if desired.

The apertures closest to the photodiode 11, such as apertures 71 and 72, or only aperture 71, can be formed to be substantially the same shape as the photodiode reducing light reflection and refraction. The light tunnel 103 acts as a guide to focus light on the photodiode 11. Thus, the lateral profiles of apertures 71, 72, 81, 82, 91, and 92 can be manipulated depending upon the desired characteristics and shape of light tunnel 103.

Figure 14:
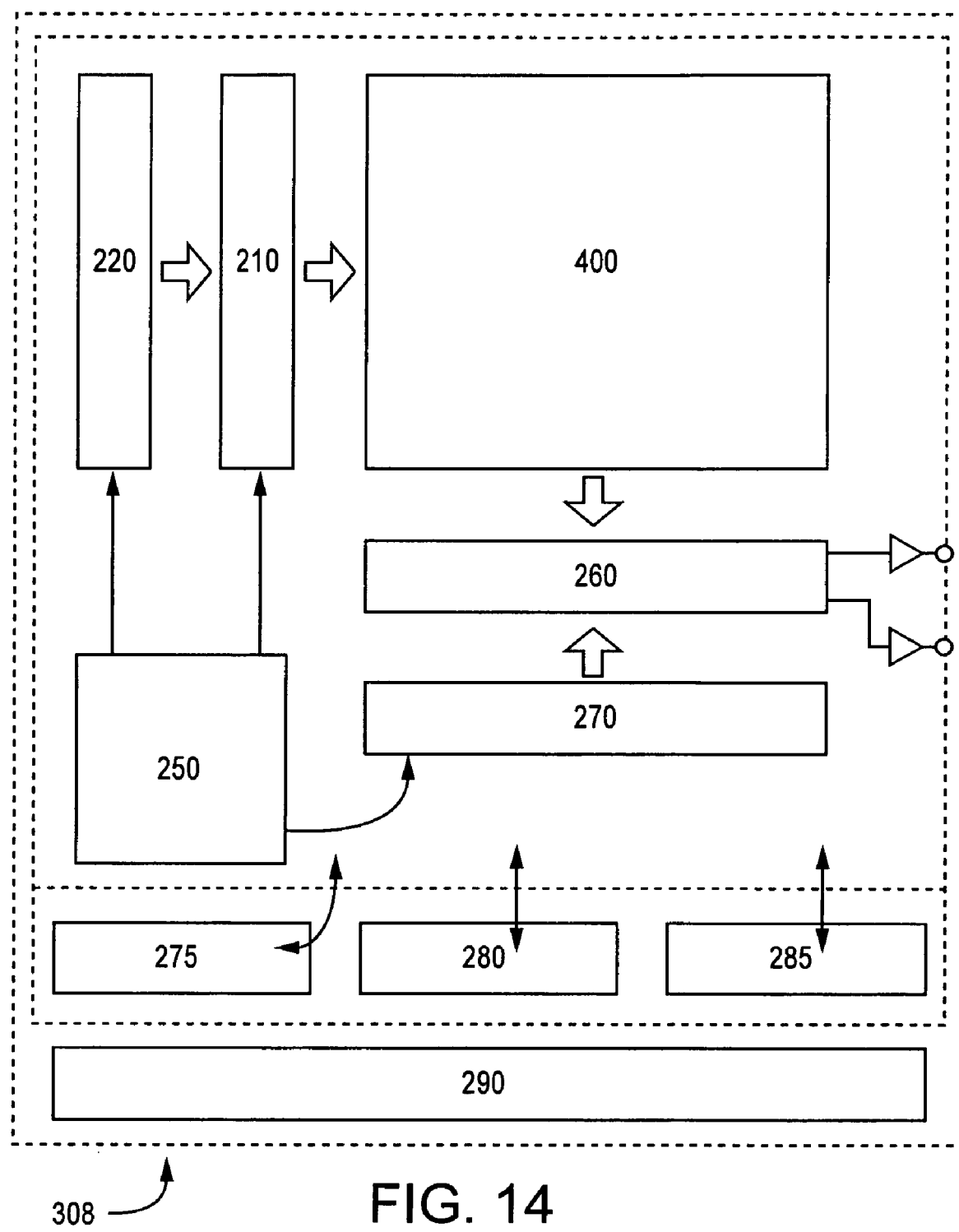
FIG. 14 shows a pixel array integrated into a CMOS imager system in accordance with the invention.

FIG. 14 illustrates a block diagram for a CMOS imager device 308 having a pixel array 400 incorporating pixel cells 100 or 200, constructed in the manner discussed above in relation to FIG. 1 through FIG. 13. Pixel array 400 comprises a plurality of pixel cells 100 or 200, arranged in a predetermined number of columns and rows. The pixel cells 100 or 200 of each row in array 400 can all be turned on at the same time by a row select line and the pixel cells 100 or 200 of each column are selectively output by a column select line. A plurality of rows and column lines are provided for the entire array 400. The row-lines are selectively activated by the row driver 210 in response to row address decoder 220 and the column select lines are selectively activated by the column driver 260 in response to column address decoder 270. Thus, a row and column address is provided for each pixel cell 100.

The CMOS imager device 308 is operated by the control circuit 250 which controls address decoders 220, 270 for selecting the appropriate row and column lines for pixel readout, and row and column driver circuitry 210, 260 which apply driving voltage to the drive transistors of the selected row and column lines. A memory 275, e.g., an SRAM, can be in communication with the array 400 and control circuit 250. A serializer module 280 and SFR (Special Function Register) device 285 can each be in communication with the control circuit 400. Optionally, a localized power source 290 can be incorporated into the imager device 308.

Typically, the signal flow in the imager device 308 would begin at the array 400 upon its receiving photo-input and generating a charge. The signal is output to a read-out circuit and then to an analog-to-digital conversion device. Then the signal is transferred to a processor, then the serializer, and then the signal can be output from the imager device to external hardware.

Figure 15:
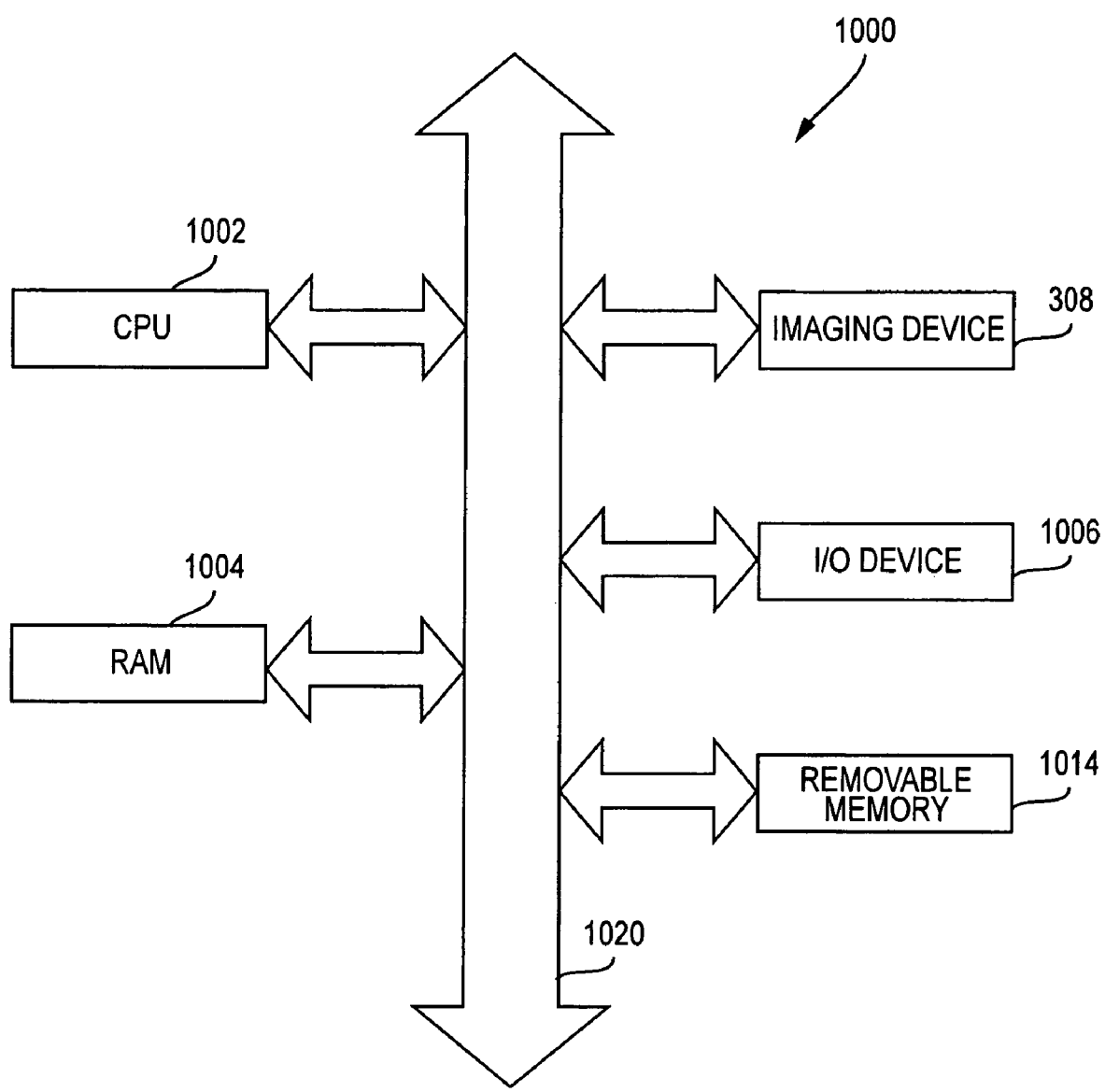
FIG. 15 shows a processor system incorporating at least one CMOS imager device, like that shown in FIG. 14, in accordance with the invention.

FIG. 15 shows a system 1000, a typical processor system modified to include an imaging device 308 (such as the imaging device 100 illustrated in FIG. 12) of the invention. The processor system 1000 is exemplary of a system having digital circuits that could include image sensor devices. Without being limiting, such a system could include a computer system, camera system, scanner, machine vision, vehicle navigation, video phone, surveillance system, auto focus system, star tracker system, motion detection system, image stabilization system, and data compression system, and other systems employing an imager.

System 1000, for example a camera system, generally comprises a central processing unit (CPU) 1002, such as a microprocessor, that communicates with an input/output (I/O) device 1006 over a bus 1020. Imaging device 308 also communicates with the CPU 1002 over the bus 1020. The processor-based system 1000 also includes random access memory (RAM) 1004, and can include removable memory 1014, such as flash memory, which also communicate with the CPU 1002 over the bus 1020. The imaging device 308 may be combined with a processor, such as a CPU, digital signal processor, or microprocessor, with or without memory storage on a single integrated circuit or on a different chip than the processor.

The processes and devices described above illustrate preferred methods and typical devices of many that could be used and produced. The above description and drawings illustrate embodiments, which achieve the objects, features, and advantages of the present invention. However, it is not intended that the present invention be strictly limited to the above-described and illustrated embodiments. Any modification, though presently unforeseeable, of the present invention that comes within the spirit and scope of the following claims should be considered part of the present invention.

What is claimed as new and desired to be protected by Letters Patent of the United States is:

1. An imager pixel comprising:
   a photosensitive region;
   a first layer formed over said photosensitive region, said first layer comprising:
      first conductive interconnect patterns, a distance between said first conductive interconnect patterns forming a first aperture; and
      first interconnect lines, a distance between said first interconnect lines forming a second aperture; and a second layer formed over said first layer, said second layer comprising:
  second conductive interconnect patterns, a distance between said second conductive interconnect patterns forming a third aperture; and
  second interconnect lines, a distance between said second interconnect lines forming a fourth aperture,
  wherein said first aperture is smaller than said third aperture.

2. An imager pixel as in claim 1, wherein said third and fourth apertures are wider than said first and second apertures.

3. An imager pixel as in claim 1, wherein the first aperture is substantially the same width as the photosensitive region.

4. An imager pixel as in claim 1, further comprising a transparent dielectric layer formed over said photosensitive region and below said first layer.

5. An imager pixel as in claim 4, further comprising an anti-reflective coating layer formed below said transparent dielectric layer.

6. An imager pixel as in claim 5, wherein said transparent dielectric layer further comprises metal contact rings.

7. An imager pixel as in claim 1, further comprising a third layer formed over said second layer, said third layer comprising third conductive interconnect patterns, a distance between said third conductive interconnect patterns forming a fifth aperture.

8. An imager pixel as in claim 7, wherein said fifth aperture is wider than said third aperture.

9. An imager pixel as in claim 8, wherein said third conductive interconnect patterns are smaller in width than said second conductive interconnect patterns.

10. An imager pixel as in claim 7, wherein said first, second, and third layers form a light tunnel comprising a stair-like shape.

11. An imager pixel as in claim 7, wherein said first, second, and third layers form a light tunnel having a shape substantially similar to the photosensitive region.

12. An imager pixel as in claim 1, wherein said first and second layers form a light tunnel comprising a stair-like shape.

13. An imager pixel as in claim 1, wherein said first and second layers form a light tunnel having a shape substantially similar to the photosensitive region.

14. A pixel cell comprising:
  a photosensor formed in a substrate below a top surface of the substrate; and
  a light tunnel for guiding light to said photosensor, said light tunnel comprising:
    a first transparent dielectric layer formed over said photosensor;
    a first metal layer formed over said transparent dielectric layer, a distance between interconnects of said first metal layer forming a first aperture;
    a second transparent dielectric layer formed over said first metal layer;
    a second metal layer formed over said second transparent dielectric layer, a distance between interconnects of said second metal layer forming a second aperture; and
    a third transparent dielectric layer formed over said second metal layer.

15. A pixel cell as in claim 14, wherein said first aperture is narrower than said second aperture.

16. A pixel cell as in claim 14, wherein said first aperture is substantially the same width as the photosensor.

17. A pixel cell as in claim 14, further comprising forming an anti-reflective coating layer below said first transparent dielectric layer.

18. A pixel cell as in claim 17, wherein said first transparent dielectric layer further comprises metal contact rings.

19. A pixel cell as in claim 14, further comprising a third metal layer formed over said third transparent dielectric layer.

20. A pixel cell as in claim 19, further comprising a fourth transparent dielectric layer formed over said third metal layer.

21. A pixel cell as in claim 19, a distance between interconnects of said third metal layer forming a third aperture, wherein said third aperture is wider than said second aperture.

22. A CMOS imager comprising:
  an array of image pixel cells arranged in rows and columns formed over a substrate, each image pixel cell comprising:
    a photosensitive region; and
    a light tunnel for guiding light to said photosensitive region, wherein said light tunnel further comprises:
      a first metallization layer formed over said photosensitive region, said first metallization layer comprising first conductive interconnect patterns, wherein a distance between said first conductive interconnect patterns forms a first aperture; and
      a second metallization layer formed over said first metallization layer, said second metallization layer comprising second conductive interconnect patterns, wherein a distance between said second conductive interconnect patterns forms a second aperture.

23. A CMOS imager as in claim 22, wherein the first aperture is narrower than said second aperture.

24. A CMOS imager as in claim 22, wherein the first aperture is substantially the same width as the photosensitive region.

25. A CMOS imager as in claim 22, further comprising forming an anti-reflective coating layer over said photosensitive region and below said first metallization layer.

26. A CMOS imager as in claim 22, further comprising a third metallization layer formed over said second metallization layer, said third metallization layer comprising third conductive interconnect patterns, wherein a distance between said third conductive interconnect patterns forms a third aperture.

27. A CMOS imager as in claim 26, wherein said third aperture is wider than said second aperture.

28. A CMOS imager as in claim 27, wherein said third conductive interconnect patterns are smaller in width than said second conductive interconnect patterns.

29. An imager system comprising:
  a processor;
  an imaging device electrically coupled to the processor, the imaging device comprising a CMOS pixel array, at least one pixel of the array comprising:
    a photosensor formed in a substrate; and
    a light tunnel for guiding light to said photosensor, said light tunnel comprising:
      a first transparent dielectric layer formed over said photosensor;
      a first metal layer formed over said transparent dielectric layer, a distance separating points of said first metal layer forming a first aperture;
      a second transparent dielectric layer formed over said first metal layer;

a second metal layer formed over said second transparent dielectric layer, a distance separating points of said second metal layer forming a second aperture; and a third transparent dielectric layer formed over said second metal layer.

30. A light tunnel structure for use in an imaging device comprising:

a first metal layer including conductive interconnects, a distance separating said conductive interconnects of said first metal layer forming a first aperture;

a first transparent dielectric layer formed over said first metal layer;

a second metal layer including conductive interconnects formed over said first transparent dielectric layer, a distance separating said conductive interconnects of said second metal layer forming a second aperture; and a second transparent dielectric layer formed over said second metal layer, wherein said second aperture is wider than said first aperture.

31. The light tunnel structure of claim 30, further comprising:

first interconnect lines formed in said first transparent dielectric layer, a distance separating said first interconnect lines forming a third aperture; and second interconnect lines formed in said second transparent dielectric layer, a distance separating said second interconnect lines forming a fourth aperture.

32. The light tunnel structure of claim 31, wherein said fourth aperture is wider than said third aperture.

33. The light tunnel structure of claim 30, further comprising:

a third metal layer including conductive interconnects, a distance separating said conductive interconnects of said third metal layer forming a third aperture; and a third transparent dielectric layer formed over said third metal layer.

34. The light tunnel structure of claim 33, wherein said third aperture is wider than said second aperture.

35. The light tunnel structure of claim 30, wherein said first and second apertures are arranged to guide and focus light on a photosensitive region.

36. The light tunnel structure of claim 35, wherein said first aperture is substantially the same width as the photosensitive region.

37. The imager system of claim 29, wherein the first aperture of the light tunnel is substantially the same width as the photosensor.

* * * * *

UNITED STATES PATENT AND TRADEMARK OFFICE
CERTIFICATE OF CORRECTION

PATENT NO. : 7,683,407 B2
APPLICATION NO. : 11/193450
DATED : March 23, 2010
INVENTOR(S) : Ulrich C. Boettiger It is certified that error appears in the above-identified patent and that said Letters Patent is hereby corrected as shown below:

In the Specification:

Column 5, line 11, "The terms 'pixel(s)' or 'pixel cell(s)' refers to" should read --The term "pixel(s)" or "pixel cell(s)" refers to--.

Column 6, lines 31-33, "Field oxide regions 8, often referred to as trench isolation regions are formed in substrate 2 separating adjacent pixel cells" should read --Field oxide regions 8, often referred to as trench isolation regions, are formed in substrate 2 separating adjacent pixel cells--.

Column 9, lines 54-55, "Consequently, the lateral profile of apertures 71, 72, 81, 82, and 91 92 can be manipulated" should read --Consequently, the lateral profile of apertures 71, 72, 81, 82, and 91 can be manipulated--.

Column 10, line 61, "about 0.8 micron's thick" should read --about 0.8 microns thick--.

Column 10, line 62, "from about 0.1 to about 1 micron's thick" should read --from about 0.1 to about 1 microns thick--.

Column 11, lines 51-55, "It is also possible, with the various structural embodiments of this invention, to entirely avoid the use of micro-lenses since the funnel-like light tunnel 103 structure, focuses light as a micro-lens does" should read --It is also possible, with the various structural embodiments of this invention, to entirely avoid the use of micro-lenses since the funnel-like light tunnel 103 structure focuses light as a micro-lens does--.

Column 12, lines 37-38, "The floating diffusion region 25, acts as a source/drain region for the transfer transistor gate 30" should read --The floating diffusion region 25 acts as a source/drain region for the transfer transistor gate 30--.

Column 13, line 33, "a $X_{gap}$" should read --an $X_{gap}$--.

Signed and Sealed this

Seventh Day of September, 2010

David J. Kappos
*Director of the United States Patent and Trademark Office*

CERTIFICATE OF CORRECTION (continued)
U.S. Pat. No. 7,683,407 B2

Column 14, lines 12-13, "The ILD 1 can then be planarized by any techniques such CMP or RIE etching techniques" should read --The ILD 1 can then be planarized by any techniques such as CMP or RIE etching techniques--.

Column 15, lines 8-10, "The ILD 1 can then be planarized by any techniques such CMP or RIE etching techniques" should read --The ILD 1 can then be planarized by any techniques such as CMP or RIE etching techniques--.